US012670670B2

(12) United States Patent
Shelton, IV et al.

(10) Patent No.: US 12,670,670 B2
(45) Date of Patent: Jun. 30, 2026

(54) MIXING DIRECTLY VISUALIZED WITH RENDERED ELEMENTS TO DISPLAY BLENDED ELEMENTS AND ACTIONS HAPPENING ON-SCREEN AND OFF-SCREEN

(71) Applicant: Cilag GmbH International, Zug (CH)

(72) Inventors: Frederick E. Shelton, IV, Hillsboro, OH (US); Shane R. Adams, Lebanon, OH (US); Matthew D. Cowperthwait, Cincinnati, OH (US); Kevin M. Fiebig, Cincinnati, OH (US); Jason L. Harris, Lebanon, OH (US); Cory G. Kimball, Hamilton, OH (US); Monica L. Z. Rivard, Cincinnati, OH (US); Leonardo N. Rossoni, Rahway, NJ (US); Risto Kojcev, Santa Clara, CA (US); Felix J. Bork, Schnürpflingen (DE)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/688,653

(22) Filed: Mar. 7, 2022

(65) Prior Publication Data

US 2022/0331013 A1      Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.
*A61B 90/00*          (2016.01)
*A61B 34/00*          (2016.01)
(Continued)

(52) U.S. Cl.
CPC .............. *G06T 11/00* (2013.01); *A61B 34/20* (2016.02); *A61B 34/25* (2016.02); *A61B 34/30* (2016.02);
(Continued)

(58) Field of Classification Search
CPC . A61B 34/20; A61B 2090/365; A61B 90/361; A61B 90/37; A61B 90/39;
(Continued)

(56) References Cited

U.S. PATENT DOCUMENTS 4,171,700 A      10/1979   Farin
4,849,752 A       7/1989   Bryant
(Continued)

FOREIGN PATENT DOCUMENTS

CA          3003058 A1      5/2017
CN        112603496 A      4/2021
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Jason M Ip
(74) *Attorney, Agent, or Firm* — Condo Roccia Koptiw LLP

(57)          ABSTRACT

Apparatuses, systems, and method for mixed reality visualization are disclosed herein. In one aspect, a method for mixed reality visualization includes capturing, by a first camera of a first visualization system, an image of an object in a surgical field, wherein a first portion of the object is outside of a field of view of the first camera; tracking, by a tracking system, a position of a second portion of the object; determining, by a surgical hub, an attribute of the object
(Continued)

based on the tracked position of the second portion of the object, wherein the attribute of the object is related to the first portion of the object outside of a field of view of the camera; and displaying, by an augmented reality display device, the captured image of the object in the surgical field and a graphic based on the attribute of the object.

14 Claims, 17 Drawing Sheets

(51) Int. Cl.

| | |
|---|---|
| A61B 34/20 | (2016.01) |
| A61B 34/30 | (2016.01) |
| A61B 34/32 | (2016.01) |
| G06F 3/14 | (2006.01) |
| G06F 3/147 | (2006.01) |
| G06T 7/00 | (2017.01) |
| G06T 7/20 | (2017.01) |
| G06T 11/00 | (2006.01) |
| G06T 19/00 | (2011.01) |
| G06V 20/20 | (2022.01) |
| G08B 21/18 | (2006.01) |
| G16H 20/40 | (2018.01) |
| G16H 40/67 | (2018.01) |
| H04L 9/40 | (2022.01) |
| H04L 67/12 | (2022.01) |
| H04W 24/10 | (2009.01) |
| H04W 76/14 | (2018.01) |
| A61B 34/10 | (2016.01) |

(52) U.S. Cl.
CPC .............. *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 19/006* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2090/365* (2016.02); *A61B 2090/368* (2016.02); *A61B 2090/371* (2016.02); *A61B 2090/372* (2016.02); *A61B 2090/373* (2016.02); *A61B 2090/3937* (2016.02); *A61B 2090/3975* (2016.02); *G06T 2207/10028* (2013.01); *G06T 2207/30024* (2013.01); *G06T 2210/41* (2013.01)

(58) Field of Classification Search
CPC .... A61B 2034/2055; A61B 2034/2072; A61B 2090/371; A61B 2090/373; A61B 2090/3937; A61B 2090/3975; G06T 7/20; G06T 19/006; G06T 2207/10028; G06T 2207/30024
See application file for complete search history.

(56) References Cited

U.S. PATENT DOCUMENTS

| | | | |
|---|---|---|---|
| D303,787 | S | 10/1989 | Messenger et al. |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,425,375 | A | 6/1995 | Chin et al. |
| D379,346 | S | 5/1997 | Mieki |
| 5,690,504 | A | 11/1997 | Scanlan et al. |
| 5,693,042 | A | 12/1997 | Boiarski et al. |
| 5,724,468 | A | 3/1998 | Leone et al. |
| 6,049,467 | A | 4/2000 | Tamarkin et al. |
| 6,055,458 | A | 4/2000 | Cochran et al. |
| D431,811 | S | 10/2000 | Nishio et al. |
| 6,179,136 | B1 | 1/2001 | Kluge et al. |
| 6,269,411 | B1 | 7/2001 | Reasoner |
| 6,288,606 | B1 | 9/2001 | Ekman et al. |
| 6,416,471 | B1 | 7/2002 | Kumar et al. |
| 6,501,485 | B1 | 12/2002 | Dash et al. |
| 6,546,270 | B1 | 4/2003 | Goldin et al. |
| 6,584,358 | B2 | 6/2003 | Carter et al. |
| 6,611,793 | B1 | 8/2003 | Burnside et al. |
| 6,731,514 | B2 | 5/2004 | Evans |
| 6,760,218 | B2 | 7/2004 | Fan |
| 6,839,238 | B2 | 1/2005 | Derr et al. |
| 6,843,657 | B2 | 1/2005 | Driscoll et al. |
| 6,913,471 | B2 | 7/2005 | Smith |
| 7,009,511 | B2 | 3/2006 | Mazar et al. |
| 7,044,949 | B2 | 5/2006 | Orszulak et al. |
| 7,074,205 | B1 | 7/2006 | Duffy et al. |
| 7,134,994 | B2 | 11/2006 | Alpert et al. |
| 7,171,784 | B2 | 2/2007 | Eenigenburg |
| 7,217,269 | B2 | 5/2007 | El-Galley et al. |
| 7,252,664 | B2 | 8/2007 | Nasab et al. |
| 7,331,699 | B2 | 2/2008 | Gawalkiewicz et al. |
| 7,344,532 | B2 | 3/2008 | Goble et al. |
| 7,353,068 | B2 | 4/2008 | Tanaka et al. |
| 7,408,439 | B2 | 8/2008 | Wang et al. |
| D579,876 | S | 11/2008 | Novotney et al. |
| D583,328 | S | 12/2008 | Chiang |
| 7,496,418 | B2 | 2/2009 | Kim et al. |
| D589,447 | S | 3/2009 | Sasada et al. |
| 7,500,747 | B2 | 3/2009 | Howell et al. |
| 7,518,502 | B2 | 4/2009 | Austin et al. |
| 7,563,259 | B2 | 7/2009 | Takahashi |
| 7,601,149 | B2 | 10/2009 | DiCarlo et al. |
| 7,637,907 | B2 | 12/2009 | Blaha |
| 7,656,671 | B2 | 2/2010 | Liu et al. |
| 7,757,028 | B2 | 7/2010 | Druke et al. |
| D631,252 | S | 1/2011 | Leslie |
| 7,932,826 | B2 | 4/2011 | Fritchie et al. |
| 7,945,065 | B2 | 5/2011 | Menzl et al. |
| 7,945,342 | B2 | 5/2011 | Tsai et al. |
| 7,982,776 | B2 | 7/2011 | Dunki-Jacobs et al. |
| 7,995,045 | B2 | 8/2011 | Dunki-Jacobs |
| 8,019,094 | B2 | 9/2011 | Hsieh et al. |
| 8,086,008 | B2 | 12/2011 | Coste-maniere et al. |
| D655,678 | S | 3/2012 | Kobayashi et al. |
| D657,368 | S | 4/2012 | Magee et al. |
| 8,239,066 | B2 | 8/2012 | Jennings et al. |
| D667,838 | S | 9/2012 | Magee et al. |
| D675,164 | S | 1/2013 | Kobayashi et al. |
| D676,392 | S | 2/2013 | Gassauer |
| D678,196 | S | 3/2013 | Miyauchi et al. |
| D678,304 | S | 3/2013 | Yakoub et al. |
| 8,423,182 | B2 | 4/2013 | Robinson et al. |
| D687,146 | S | 7/2013 | Juzkiw et al. |
| 8,504,136 | B1 | 8/2013 | Sun et al. |
| 8,540,709 | B2 | 9/2013 | Allen |
| 8,567,393 | B2 | 10/2013 | Hickle et al. |
| D704,839 | S | 5/2014 | Juzkiw et al. |
| 8,795,001 | B1 | 8/2014 | Lam et al. |
| 8,819,581 | B2 | 8/2014 | Nakamura et al. |
| D716,333 | S | 10/2014 | Chotin et al. |
| 8,917,513 | B1 | 12/2014 | Hazzard |
| 8,920,186 | B2 | 12/2014 | Shishikura |
| 8,923,012 | B2 | 12/2014 | Kaufman et al. |
| 8,968,296 | B2 | 3/2015 | McPherson |
| 8,986,288 | B2 | 3/2015 | Konishi |
| 9,017,326 | B2 | 4/2015 | Dinardo et al. |
| D729,267 | S | 5/2015 | Yoo et al. |

(56)  References Cited

U.S. PATENT DOCUMENTS

| | | |
|---|---|---|
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,085 B2 | 10/2015 | Juzkiw et al. |
| 9,168,091 B2 | 10/2015 | Janssen et al. |
| 9,198,711 B2 | 12/2015 | Joseph |
| 9,220,570 B2 | 12/2015 | Kim et al. |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,503,681 B1 | 11/2016 | Popescu et al. |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,629,176 B2 | 4/2017 | Guo et al. |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,892,564 B1 | 2/2018 | Cvetko et al. |
| 9,907,196 B2 | 2/2018 | Susini et al. |
| 9,935,794 B1 | 4/2018 | Cao et al. |
| 9,971,395 B2 | 5/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,019 B2 | 1/2019 | Nawana et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,262,453 B2 | 4/2019 | Mountney et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,610,310 B2 | 4/2020 | Todd et al. |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| 11,006,100 B1 | 5/2021 | Douglas |
| D924,139 S | 7/2021 | Jayme |
| 11,056,244 B2 | 7/2021 | Shelton, IV et al. |
| 11,058,497 B2 | 7/2021 | Altmann et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,114,199 B2 | 9/2021 | Moctezuma De La Barrera |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,341,726 B2 | 5/2022 | Tsuda et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 11,823,374 B2 | 11/2023 | Schneider et al. |
| 11,836,863 B2 | 12/2023 | Flexman et al. |
| 12,349,861 B2 | 7/2025 | Charles et al. |
| 2001/0029315 A1 | 10/2001 | Sakurai et al. |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0082542 A1 | 4/2006 | Morita et al. |

(56)  References Cited

U.S. PATENT DOCUMENTS

| | | |
|---|---|---|
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0211930 A1 | 9/2007 | Dolwick et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0131929 A1 | 5/2009 | Shimizu |
| 2009/0192524 A1* | 7/2009 | Itkowitz ................. B25J 9/1692 |
| | | 606/130 |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0042010 A1 | 2/2010 | Dekker et al. |
| 2010/0053213 A1 | 3/2010 | Ishida et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0105895 A1 | 5/2011 | Kornblau et al. |
| 2011/0118748 A1 | 5/2011 | Itkowitz |
| 2011/0125149 A1 | 5/2011 | El-Galley et al. |
| 2011/0130689 A1 | 6/2011 | Cohen et al. |
| 2011/0190588 A1 | 8/2011 | Mckay |
| 2011/0245630 A1 | 10/2011 | St. Pierre et al. |
| 2011/0273465 A1 | 11/2011 | Konishi et al. |
| 2011/0298814 A1 | 12/2011 | Mathew et al. |
| 2011/0306840 A1 | 12/2011 | Allen et al. |
| 2012/0029304 A1 | 2/2012 | Medina et al. |
| 2012/0082036 A1 | 4/2012 | Abedi et al. |
| 2012/0116380 A1 | 5/2012 | Madan et al. |
| 2012/0132661 A1 | 5/2012 | Gu et al. |
| 2013/0031201 A1 | 1/2013 | Kagan et al. |
| 2013/0038707 A1 | 2/2013 | Cunningham et al. |
| 2013/0176220 A1 | 7/2013 | Merschon et al. |
| 2013/0197357 A1 | 8/2013 | Green et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2013/0303851 A1 | 11/2013 | Griffith et al. |
| 2013/0321159 A1 | 12/2013 | Schofield et al. |
| 2014/0009894 A1 | 1/2014 | Yu |
| 2014/0052150 A1 | 2/2014 | Taylor et al. |
| 2014/0058714 A1 | 2/2014 | Boyer |
| 2014/0087573 A1 | 3/2014 | Kroeckel |
| 2014/0155721 A1 | 6/2014 | Hauck et al. |
| 2014/0179997 A1 | 6/2014 | Grunberg et al. |
| 2014/0194683 A1 | 7/2014 | Nakaguchi |
| 2014/0221740 A1 | 8/2014 | Kawula et al. |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0343358 A1 | 11/2014 | Hameed et al. |
| 2015/0019259 A1 | 1/2015 | Qureshi et al. |
| 2015/0057575 A1 | 2/2015 | Tsusaka et al. |
| 2015/0070388 A1 | 3/2015 | Sheaffer et al. |
| 2015/0190189 A1 | 7/2015 | Yates et al. |
| 2015/0265369 A1 | 9/2015 | Garbey et al. |
| 2015/0272575 A1 | 10/2015 | Leimbach et al. |
| 2015/0289929 A1 | 10/2015 | Toth et al. |
| 2016/0045247 A1 | 2/2016 | Heim et al. |
| 2016/0058286 A1 | 3/2016 | Joshua et al. |
| 2016/0066184 A1 | 3/2016 | Bhargav-Spantzel et al. |
| 2016/0074096 A1 | 3/2016 | Lieu |
| 2016/0120591 A1 | 5/2016 | Smith et al. |
| 2016/0174897 A1 | 6/2016 | Sherman |
| 2016/0225192 A1 | 8/2016 | Jones et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0090507 A1 | 3/2017 | Wiener et al. |
| 2017/0189096 A1 | 7/2017 | Danziger et al. |
| 2017/0202595 A1 | 7/2017 | Shelton, IV |
| 2017/0209225 A1 | 7/2017 | Wu |
| 2017/0251305 A1 | 8/2017 | Fathollahi |
| 2017/0252091 A1 | 9/2017 | Honda |
| 2017/0258526 A1 | 9/2017 | Lang |
| 2017/0296036 A1 | 10/2017 | Newman |
| 2017/0296213 A1 | 10/2017 | Swensgard et al. |
| 2017/0319259 A1 | 11/2017 | Dunning |
| 2017/0333275 A1 | 11/2017 | Itkowitz et al. |
| 2017/0360466 A1 | 12/2017 | Brown et al. |
| 2017/0367766 A1 | 12/2017 | Mahfouz |
| 2018/0014872 A1 | 1/2018 | Dickerson |
| 2018/0032130 A1 | 2/2018 | Meglan |
| 2018/0042659 A1 | 2/2018 | Rupp et al. |
| 2018/0043037 A1 | 2/2018 | Dalma-weiszhausz et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0092699 A1 | 4/2018 | Finley |
| 2018/0099161 A1 | 4/2018 | Honda |
| 2018/0168741 A1 | 6/2018 | Swayze et al. |
| 2018/0173323 A1 | 6/2018 | Harvey et al. |
| 2018/0221005 A1 | 8/2018 | Hamel et al. |
| 2018/0228528 A1 | 8/2018 | Fraasch et al. |
| 2018/0228555 A1 | 8/2018 | Charron et al. |
| 2018/0235441 A1 | 8/2018 | Huang et al. |
| 2018/0243573 A1 | 8/2018 | Yoder et al. |
| 2018/0262916 A1 | 9/2018 | Polley et al. |
| 2018/0263557 A1 | 9/2018 | Kahlman |
| 2018/0289338 A1 | 10/2018 | Meador et al. |
| 2018/0317826 A1 | 11/2018 | Muhsin et al. |
| 2018/0333207 A1 | 11/2018 | Moctezuma De la Barrera |
| 2018/0368930 A1 | 12/2018 | Esterberg et al. |
| 2019/0006047 A1 | 1/2019 | Gorek et al. |
| 2019/0035153 A1 | 1/2019 | Dange |
| 2019/0038362 A1* | 2/2019 | Nash ...................... A61B 34/25 |
| 2019/0069957 A1 | 3/2019 | Barral et al. |
| 2019/0104919 A1 | 4/2019 | Shelton, IV et al. |
| 2019/0117326 A1 | 4/2019 | Wada |
| 2019/0125361 A1 | 5/2019 | Shelton, IV et al. |
| 2019/0125451 A1 | 5/2019 | Srimohanarajah et al. |
| 2019/0125454 A1 | 5/2019 | Stokes et al. |
| 2019/0125455 A1 | 5/2019 | Shelton, IV et al. |
| 2019/0125459 A1 | 5/2019 | Shelton et al. |
| 2019/0183576 A1 | 6/2019 | Fahim et al. |
| 2019/0183591 A1 | 6/2019 | Johnson et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201046 A1 | 7/2019 | Shelton, IV et al. |
| 2019/0201102 A1 | 7/2019 | Shelton, IV et al. |
| 2019/0201114 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201127 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0205001 A1 | 7/2019 | Messerly et al. |
| 2019/0206004 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2019/0282307 A1 | 9/2019 | Azizian et al. |
| 2019/0290297 A1 | 9/2019 | Haider et al. |
| 2019/0348169 A1 | 11/2019 | Gibby et al. |

(56) References Cited

U.S. PATENT DOCUMENTS

| | | |
|---|---|---|
| 2019/0371012 A1 | 12/2019 | Flexman et al. |
| 2020/0004487 A1 | 1/2020 | Hanajima et al. |
| 2020/0015895 A1 | 1/2020 | Frielinghaus et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015902 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015924 A1 | 1/2020 | Scheib et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0093357 A1 | 3/2020 | Scott et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237031 A1 | 7/2020 | Daniels et al. |
| 2020/0237452 A1 | 7/2020 | Wolf et al. |
| 2020/0246084 A1 | 8/2020 | Azizian |
| 2020/0268469 A1 | 8/2020 | Wolf et al. |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0315707 A1 | 10/2020 | Venkataraman |
| 2020/0315734 A1 | 10/2020 | El Amm |
| 2020/0322516 A1 | 10/2020 | Doser et al. |
| 2020/0342228 A1 | 10/2020 | Prevrhal et al. |
| 2020/0359892 A1 | 11/2020 | Rollins et al. |
| 2020/0384287 A1 | 12/2020 | Hetz |
| 2020/0405529 A1 | 12/2020 | Taylor et al. |
| 2021/0000564 A1 | 1/2021 | Amanatullah et al. |
| 2021/0015343 A1 | 1/2021 | Uyama et al. |
| 2021/0093390 A1 | 4/2021 | Poltaretskyi et al. |
| 2021/0121246 A1 | 4/2021 | Gudalo |
| 2021/0128254 A1 | 5/2021 | Geric et al. |
| 2021/0158779 A1* | 5/2021 | Singh ..................... G06T 11/00 |
| 2021/0169578 A1 | 6/2021 | Calloway et al. |
| 2021/0169581 A1 | 6/2021 | Calloway et al. |
| 2021/0174956 A1* | 6/2021 | McGinley .............. G16H 40/67 |
| 2021/0192759 A1 | 6/2021 | Lang |
| 2021/0193681 A1 | 6/2021 | Baek |
| 2021/0196381 A1 | 7/2021 | Eckert et al. |
| 2021/0196383 A1 | 7/2021 | Shelton, IV et al. |
| 2021/0196425 A1 | 7/2021 | Shelton et al. |
| 2021/0203889 A1 | 7/2021 | Fung et al. |
| 2021/0205020 A1 | 7/2021 | Shelton, IV et al. |
| 2021/0212717 A1 | 7/2021 | Yates et al. |
| 2021/0236755 A1 | 8/2021 | King et al. |
| 2021/0259789 A1 | 8/2021 | Wright et al. |
| 2021/0264680 A1 | 8/2021 | Cvetko et al. |
| 2021/0267664 A1 | 9/2021 | Lennartz et al. |
| 2021/0306691 A1 | 9/2021 | Thomas et al. |
| 2021/0307861 A1 | 10/2021 | Hufford et al. |
| 2021/0313052 A1 | 10/2021 | Makrinich et al. |
| 2021/0333864 A1 | 10/2021 | Harvey et al. |
| 2021/0346092 A1 | 11/2021 | Redmond et al. |
| 2021/0369394 A1 | 12/2021 | Braido et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0142573 A1 | 5/2022 | Li et al. |
| 2022/0151704 A1 | 5/2022 | Nikou |
| 2022/0155910 A1 | 5/2022 | Jeong |
| 2022/0160428 A1 | 5/2022 | Murray et al. |
| 2022/0188545 A1 | 6/2022 | Nagar et al. |
| 2022/0237878 A1 | 7/2022 | Tartz et al. |
| 2022/0257333 A1 | 8/2022 | Haider |
| 2022/0261056 A1 | 8/2022 | Motoi et al. |
| 2022/0283631 A1 | 9/2022 | Peng |
| 2022/0287676 A1 | 9/2022 | Steines et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2022/0387128 A1 | 12/2022 | Bail et al. |
| 2023/0038130 A1 | 2/2023 | Cvetko et al. |
| 2023/0061534 A1 | 3/2023 | Stopek |
| 2023/0071306 A1 | 3/2023 | Miller et al. |
| 2023/0072423 A1 | 3/2023 | Osborn et al. |
| 2023/0121709 A1 | 4/2023 | Xu et al. |
| 2023/0157757 A1 | 5/2023 | Braido et al. |
| 2023/0157762 A1 | 5/2023 | Braido et al. |
| 2024/0130795 A1 | 4/2024 | Clayton et al. |
| 2024/0138931 A1 | 5/2024 | Lefauconnier |
| 2024/0176441 A1 | 5/2024 | Yang et al. |
| 2024/0325085 A1 | 10/2024 | Ryan et al. |

FOREIGN PATENT DOCUMENTS

| | | | |
|---|---|---|---|
| EP | 0408160 A1 | 1/1991 |
| EP | 0473987 A1 | 3/1992 |
| EP | 0929263 B1 | 7/1999 |
| EP | 1006892 B1 | 6/2009 |
| EP | 2942023 A2 | 11/2015 |
| EP | 3053279 A1 | 8/2016 |
| EP | 3387982 A1 | 10/2018 |
| JP | 2000-271145 A | 10/2000 |
| JP | 2001029353 A | 2/2001 |
| JP | 2006-149560 A | 6/2006 |

(56) References Cited

FOREIGN PATENT DOCUMENTS

| | | | |
|---|---|---|---|
| JP | 2007-007041 | A | 1/2007 |
| JP | 2007-029232 | A | 2/2007 |
| JP | 2021-045341 | A | 3/2021 |
| WO | WO-0112089 | A1 | 2/2001 |
| WO | WO-2008053485 | A1 | 5/2008 |
| WO | 2014/010177 | A1 | 1/2014 |
| WO | WO-2014031800 | A1 | 2/2014 |
| WO | WO-2014071184 | A1 | 5/2014 |
| WO | WO-2015047693 | A1 | 4/2015 |
| WO | 2016/013636 | A1 | 1/2016 |
| WO | 2016154557 | A1 | 9/2016 |
| WO | WO-2017058617 | A2 | 4/2017 |
| WO | 2017/099153 | A1 | 6/2017 |
| WO | 2017/221367 | A1 | 12/2017 |
| WO | WO-2018116247 | A1 | 6/2018 |
| WO | WO-2019215354 | A1 | 11/2019 |
| WO | 2020112217 | A1 | 6/2020 |
| WO | 2020180917 | A1 | 9/2020 |
| WO | WO-2021044136 | A1 | 3/2021 |
| WO | 2021146313 | A1 | 7/2021 |

OTHER PUBLICATIONS

IEEE Std 802.3-2012 (Revision of IEEE Std 802.3-2008, published Dec. 28, 2012.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

Vávra, et al., "Recent Development of Augmented Reality in Surgery: A Review", Journal of Healthcare Engineering, vol. 2017, Article ID 4574172, Aug. 21, 2017, pp. 1-9.

Zherdeva, et al., "Virtual Scalpel Simulation In The VR and AR Environments", Proceedings Of SPIE, vol. 11310, Feb. 19, 2020, 7 pages.

International Search Report and Written Opinion received for PCT Application No. PCT/IB2022/053360, Mailed on Jul. 4, 2022, 12 pages.

International Search Report and Written Opinion received for PCT Application No. PCT/IB2022/053362, Mailed on Jul. 1, 2022, 13 pages.

International Search Report and Written Opinion received for PCT Application No. PCT/IB2022/053363, Mailed on Jun. 30, 2022, 14 pages.

International Search Report and Written Opinion received for PCT Application No. PCT/IB2022/053364, Mailed on Jul. 8, 2022, 11 pages.

International Search Report and Written Opinion received for PCT Application No. PCT/IB2022/053365, Mailed on Jul. 4, 2022, 16 pages.

International Search Report and Written Opinion received for PCT Application No. PCT/IB2022/053369, Mailed on Jul. 13, 2022, 12 pages.

International Search Report and Written Opinion received for PCT Application No. PCT/IB2022/053370, Mailed on Jul. 15, 2022, 14 pages.

International Search Report and Written Opinion received for PCT Application No. PCT/IB2022/053371, Mailed on Jul. 5, 2022, 12 pages.

International Search Report and Written Opinion received for PCT Application No. PCT/IB2022/053375, Mailed on Oct. 4, 2022, 22 pages.

International Search Report and Written Opinion received for PCT Application No. PCT/IB2022/053377, Mailed on Jun. 22, 2022, 12 pages.

International Search Report and Written Opinion received for PCT Application No. PCT/IB2022/053378, Mailed on Jul. 7, 2022, 13 pages.

Invitation to Pay Additional Fees received for PCT Application No. PCT/IB2022/053375, Mailed on Jul. 15, 2022, 11 pages.

Kaushik et al., "Emerging Thermal Technology Enabled Augmented Reality", Advanced Functional Materials, vol. 31, No. 39, Feb. 17, 2021., pp. 1-27.

* cited by examiner

Figure 11:
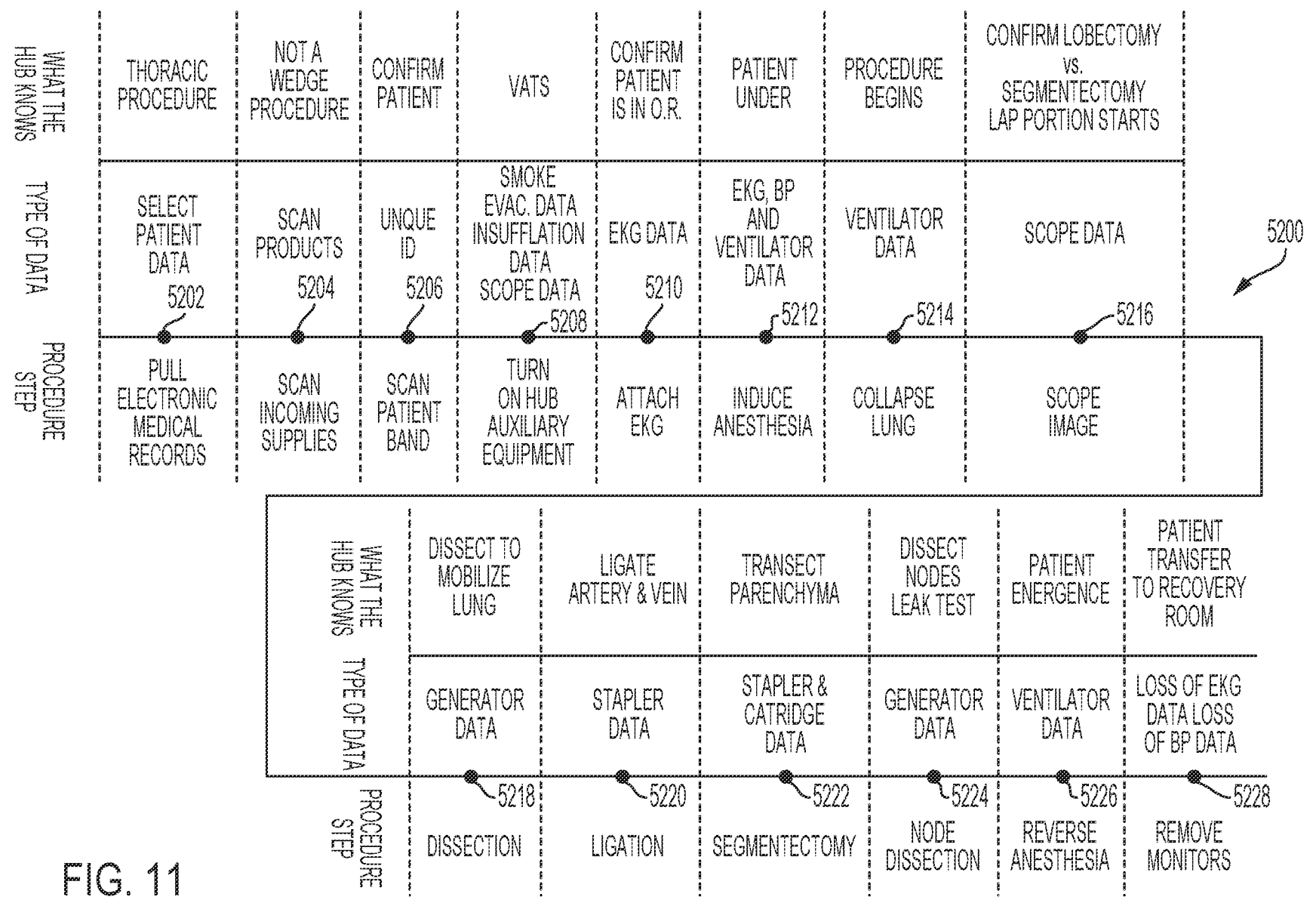

| WHAT THE HUB KNOWS | TYPE OF DATA | PROCEDURE STEP |
|---|---|---|
| THORACIC PROCEDURE | SELECT PATIENT DATA 5202 | PULL ELECTRONIC MEDICAL RECORDS |
| NOT A WEDGE PROCEDURE | SCAN PRODUCTS 5204 | SCAN INCOMING SUPPLIES |
| CONFIRM PATIENT | UNIQUE ID 5206 | SCAN PATIENT BAND |
| VATS | SMOKE EVAC. DATA INSUFFLATION DATA SCOPE DATA 5208 | TURN ON HUB AUXILIARY EQUIPMENT |
| CONFIRM PATIENT IS IN O.R. | EKG DATA 5210 | ATTACH EKG |
| PATIENT UNDER | EKG, BP AND VENTILATOR DATA 5212 | INDUCE ANESTHESIA |
| PROCEDURE BEGINS | VENTILATOR DATA 5214 | COLLAPSE LUNG |
| CONFIRM LOBECTOMY vs. SEGMENTECTOMY LAP PORTION STARTS | SCOPE DATA 5216 | SCOPE IMAGE |

| WHAT THE HUB KNOWS | TYPE OF DATA | PROCEDURE STEP |
|---|---|---|
| DISSECT TO MOBILIZE LUNG | GENERATOR DATA 5218 | DISSECTION |
| LIGATE ARTERY & VEIN | STAPLER DATA 5220 | LIGATION |
| TRANSECT PARENCHYMA | STAPLER & CATRIDGE DATA 5222 | SEGMENTECTOMY |
| DISSECT NODES LEAK TEST | GENERATOR DATA 5224 | NODE DISSECTION |
| PATIENT EMERGENCE | VENTILATOR DATA 5226 | REVERSE ANESTHESIA |
| PATIENT TRANSFER TO RECOVERY ROOM | LOSS OF EKG DATA LOSS OF BP DATA 5228 | REMOVE MONITORS |

| Object Interaction | Time Stamp | Position (X,Y,Z) | Glove ID | Device ID | Device Portion | Action | Tracking Source |
|---|---|---|---|---|---|---|---|
| Glove to Glove connection<br><br>(two surgeons) | 1621964600 | (0,0,0)<br>(0,0,0) | 123 | 124 | N/A | Initiation | Wearable |
| | 1621964605 | (0,0,0)<br>(0,0,0) | 125 | 126 | N/A | Initiation | Wearable |
| No surgeon is touching the trocar | 1621964666 | (10.1,200.3,50.9)<br>(12.2, 89.1,70.4) | 0 | Trocar 1 | N/A | Standby | Camera |
| Single surgeon One surgeon | 1621965000 | (12.1,201.4,40.1)<br>(10.2, 69.1,60.4) | 123 | Trocar 1 | N/A | In-use | Camera |
| | 1621965000 | (12.1,201.4,40.1)<br>(10.2, 69.1,60.4) | 123 | Endocutter 1 | Handle | Clamping (12lbf) | Wearable |
| Multiple surgeon with single surgeon holding device | 1621965000 | (12.1,201.4,40.1)<br>(10.2, 69.1,60.4) | 123 | Trocar 1 | N/A | In-use | Camera |
| | 1621965000 | (12.1,201.4,40.1)<br>(10.2, 69.1,60.4) | 123 | Endocutter 1 | Handle | Device Unclamped | Wearable |
| Multiple surgeon Line 1 with | 1621965014 | (12.0,205.4,39.1)<br>(11.2, 59.1,59.4) | 123,125 | Trocar 1 | N/A | In-use | Camera |
| | 1621965014 | (12.0,205.4,39.1)<br>(11.2, 59.1,59.4) | 123,125 | Endocutter 1 | Handle,Handle | Hand-off Initiated | Camera |
| Multiple surgeon Line 2 middle of switch | 1621965016 | (12.0,205.4,39.1)<br>(11.2, 59.1,59.4) | 125,123 | Trocar 1 | N/A | In-use | Camera |
| | 1621965016 | (12.0,205.4,39.1)<br>(11.2, 59.1,59.4) | 125,123 | Endocutter 1 | Handle,Handle | Hand-off | Camera |
| Multiple surgeon Line 2 after of switch | 1621965017 | (11.0,204.4,38.1)<br>(10.2, 57.1,58.4) | 125 | Trocar 1 | N/A | In-use | Camera |
| | 1621965017 | (11.0,204.4,38.1)<br>(10.2, 57.1,58.4) | 125 | Endocutter 1 | Handle | Hand-off Complete | Combination |
| Example of multi part device | 1621965030 | (9.0,210.4,35.1)<br>(16.2, 62.1,70.4) | 125,123 | Circular 1 | Handle,Shaft | Rotating Knob, AttachingAnvil | Wearable, Device (anvil detection sensor) |
| Example of unknown user | 1621965035 | (4.0,150.0,32.0)<br>(18.1,180.0,40.0) | 0 | Endocutter 1 | Device | Blue Reload Inserted | Camera |

FIG. 15

MIXING DIRECTLY VISUALIZED WITH RENDERED ELEMENTS TO DISPLAY BLENDED ELEMENTS AND ACTIONS HAPPENING ON-SCREEN AND OFF-SCREEN

CROSS-REFERENCE TO RELATED APPLICATIONS

This application claims the benefit under 35 U.S.C. § 119(e) to U.S. Provisional Patent Application No. 63/174, 674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices including energy, staplers, or combined energy and staplers. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are surgical instruments used to cut and staple tissue in a variety of surgical procedures, including bariatric, thoracic, colorectal, gynecologic, urologic and general surgery.

SUMMARY

In various aspects, the present disclosure provides a method for mixed reality visualization of a surgical system. In some aspects, the method includes capturing, by a first camera of a first visualization system, an image of an object in a surgical field, wherein a first portion of the object is outside of a field of view of the first camera; tracking, by a tracking system, a position of a second portion of the object; determining, by a surgical hub, an attribute of the object based on the tracked position of the second portion of the object, wherein the attribute of the object is related to the first portion of the object outside of a field of view of the camera; and displaying, by an augmented reality display device, the captured image of the object in the surgical field and a graphic based on the attribute of the object. In one aspect, the object includes a surgical instrument, patient tissue, or a user, or a combination thereof.

In various aspects, the present disclosure provides a surgical system for mixed reality visualization. In some aspects, the system includes a first visualization system including a first camera configured to capture an image of an object in a surgical field, wherein a first portion of the object is outside of a field of view of the camera; a first tracking system configured to track a position of a second portion the object; a surgical hub configured to determine an attribute of the object based on the tracked position of the second portion the object, wherein the attribute of the object is related to the first portion of the object outside of a field of view of the camera; and an augmented reality display device configured to display the captured image of the object in the surgical field and a graphic based on the attribute of the object. In one aspect, the object includes a surgical instrument, patient tissue, a user, or a combination thereof.

FIGURES

The various aspects described herein, both as to organization and methods of operation, together with further objects and advantages thereof, may best be understood by reference to the following description, taken in conjunction with the accompanying drawings as follows.

FIG. 11 illustrates a timeline of a situational awareness surgical procedure, according to one aspect of this disclosure.

FIG. 15 is a table of exemplary tracked object interactions determined by a surgical hub based on data generated by a tracking system, according to one aspect of this disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Figure 1:
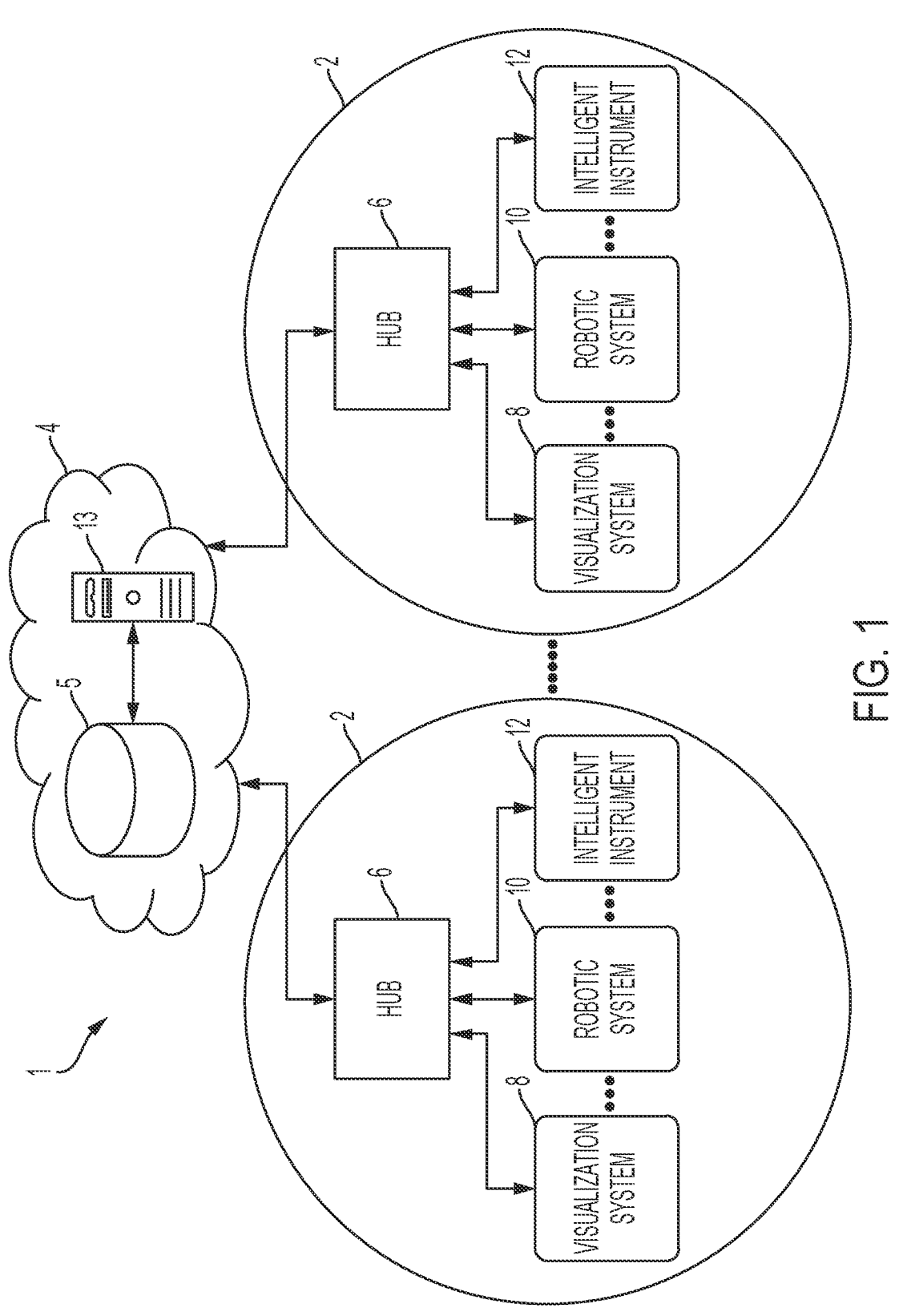
FIG. 1 is a block diagram of a computer-implemented interactive surgical system, according to one aspect of this disclosure.

Applicant of the present application owns the following U.S. patent applications filed concurrently herewith, the disclosures of each of which is herein incorporated by reference in its entirety:

U.S. patent application Ser. No. 17/688,589, filed Mar. 7, 2022, titled METHOD FOR INTRAOPERATIVE DISPLAY FOR SURGICAL SYSTEMS;

U.S. patent application Ser. No. 17/688,597, filed Mar. 7, 2022, titled UTILIZATION OF SURGICAL DATA VALUES AND SITUATIONAL AWARENESS TO CONTROL THE OVERLAY IN SURGICAL FIELD VIEW;

U.S. patent application Ser. No. 17/688,605, filed Mar. 7, 2022, titled SELECTIVE AND ADJUSTABLE MIXED REALITY OVERLAY IN SURGICAL FIELD VIEW;

U.S. patent application Ser. No. 17/688,615, filed Mar. 7, 2022, titled RISK BASED PRIORITIZATION OF DISPLAY ASPECTS IN SURGICAL FIELD VIEW;

U.S. patent application Ser. No. 17/688,626, filed Mar. 7, 2022, titled SYSTEMS AND METHODS FOR CONTROLLING SURGICAL DATA OVERLAY;

U.S. patent application Ser. No. 17/688,633, filed Mar. 7, 2022, titled SYSTEMS AND METHODS FOR CHANGING DISPLAY OVERLAY OF SURGICAL FIELD VIEW BASED ON TRIGGERING EVENTS;

U.S. patent application Ser. No. 17/688,638, filed Mar. 7, 2022, titled CUSTOMIZATION OF OVERLAID DATA AND CONFIGURATION;

U.S. patent application Ser. No. 17/688,641, filed Mar. 7, 2022, titled INDICATION OF THE COUPLE PAIR OF REMOTE CONTROLS WITH REMOTE DEVICES FUNCTIONS;

U.S. patent application Ser. No. 17/688,646, filed Mar. 7, 2022, titled COOPERATIVE OVERLAYS OF INTERACTING INSTRUMENTS WHICH RESULT IN BOTH OVERLAYS BEING EFFECTED;

U.S. patent application Ser. No. 17/688,651, filed Mar. 7, 2022, titled ANTICIPATION OF INTERACTIVE UTILIZATION OF COMMON DATA OVERLAYS BY DIFFERENT USERS;

U.S. patent application Ser. No. 17/688,655, filed Mar. 7, 2022, titled SYSTEM AND METHOD FOR TRACKING A PORTION OF THE USER AS A PROXY FOR NON-MONITORED INSTRUMENT;

U.S. patent application Ser. No. 17/688,656, filed Mar. 7, 2022, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;

U.S. patent application Ser. No. 17/688,660, filed Mar. 7, 2022, titled COOPERATION AMONG MULTIPLE DISPLAY SYSTEMS TO PROVIDE A HEALTHCARE USER CUSTOMIZED INFORMATION;

U.S. patent application Ser. No. 17/688,663, filed Mar. 7, 2022, titled INTRAOPERATIVE DISPLAY FOR SURGICAL SYSTEMS;

U.S. patent application Ser. No. 17/688,667, filed Mar. 7, 2022, titled ADAPTATION AND ADJUSTABILITY OR OVERLAID INSTRUMENT INFORMATION FOR SURGICAL SYSTEMS; and U.S. patent application Ser. No. 17/688,671, filed Mar. 7, 2022, titled MIXED REALITY FEEDBACK SYSTEMS THAT COOPERATE TO INCREASE EFFICIENT PERCEPTION OF COMPLEX DATA FEEDS.

Applicant of this application owns the following U.S. patent applications, the disclosure of each of which is herein incorporated by reference in its entirety:

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;

U.S. patent application Ser. No. 16/209,453, titled METHOD FOR CONTROLLING SMART ENERGY DEVICES, now U.S. Patent Publication No. US-2019-0201046-A1.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
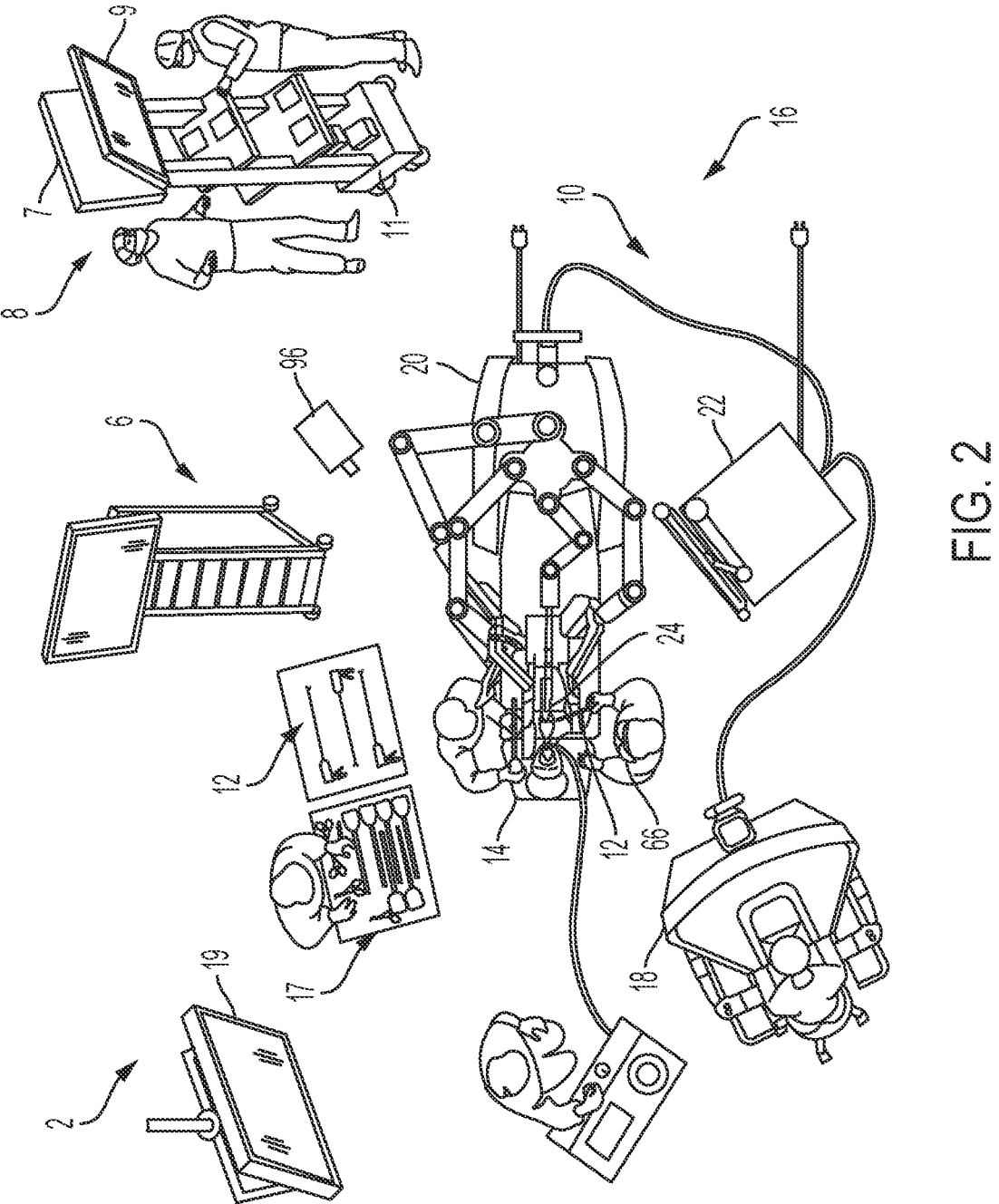
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
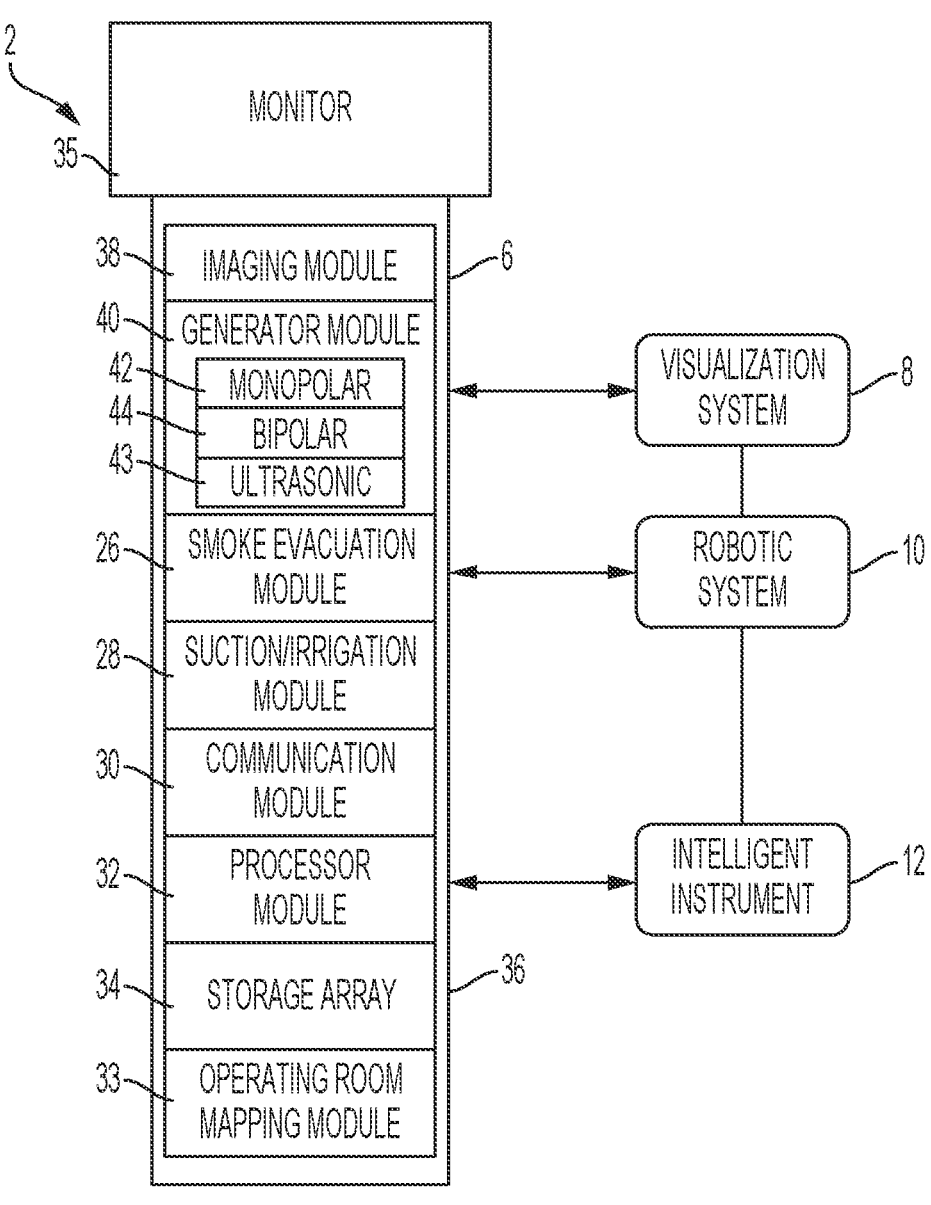
FIG. 3 is a surgical hub paired with a visualization system, a robotic system, and an intelligent instrument, according to one aspect of this disclosure.
Figure 10:
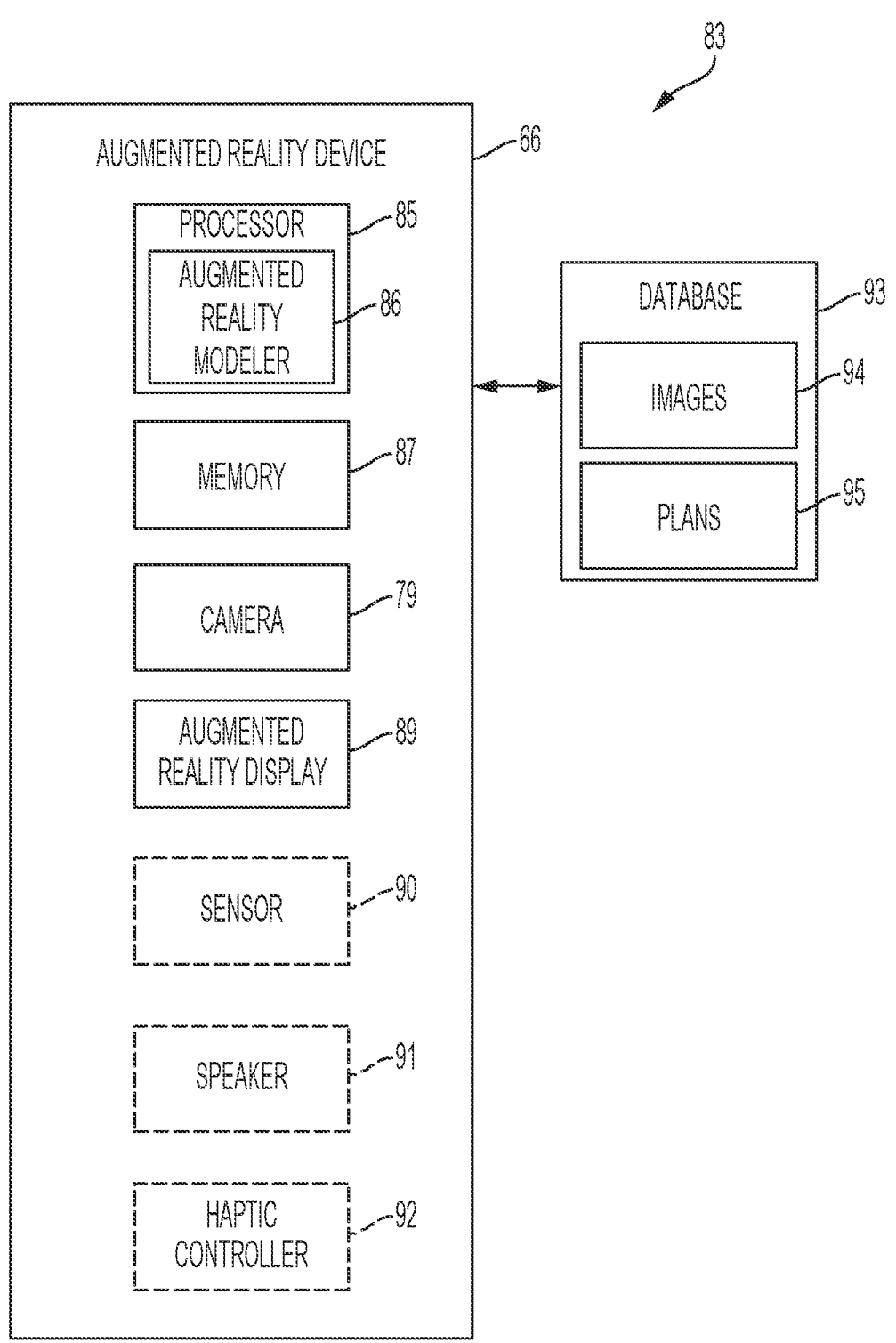
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
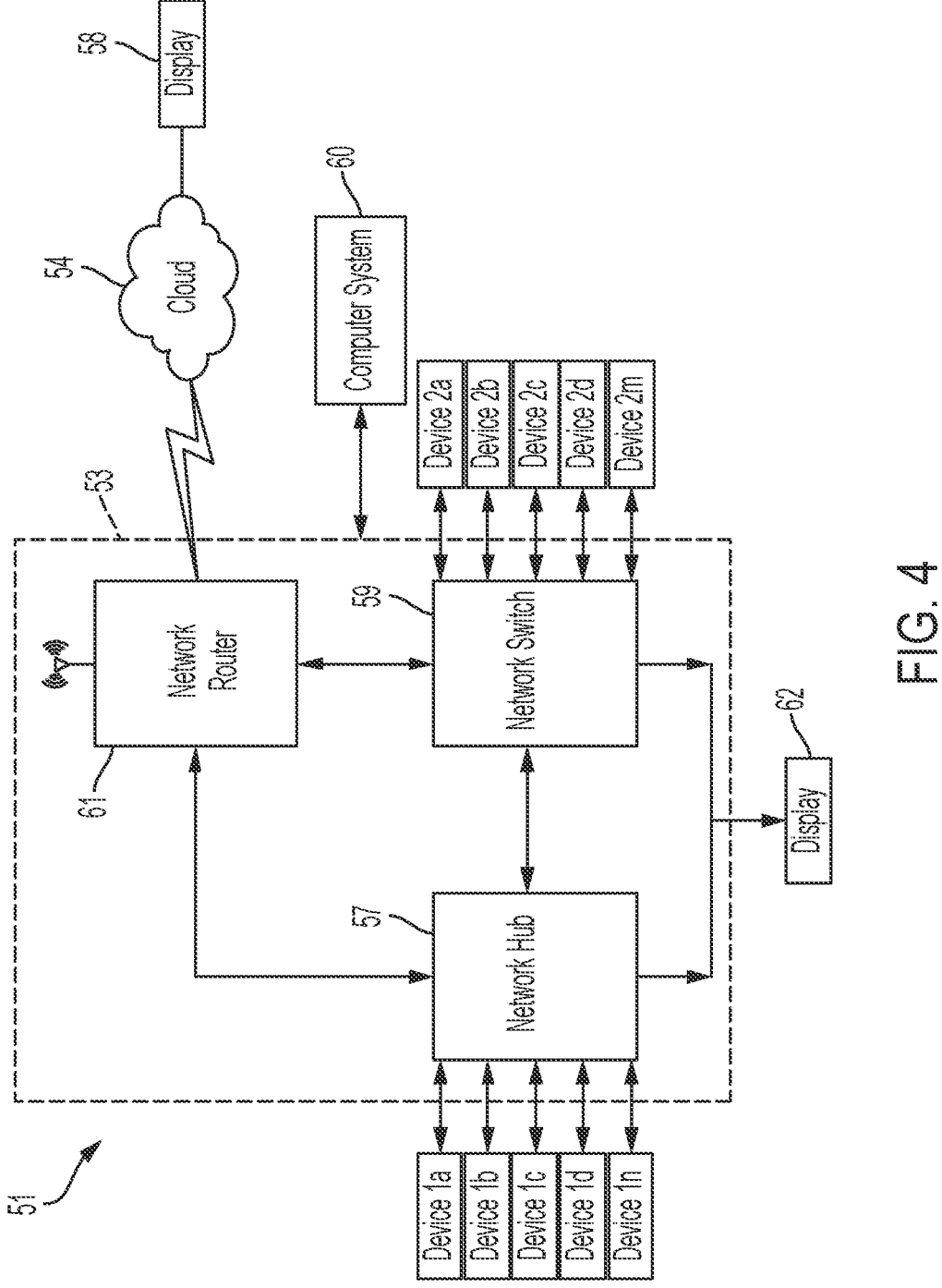
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1a-1n in the operating theater may be coupled to the modular communication hub 53. The network hub 57 and/or the network switch 59 may be coupled to a network router 61 to connect the devices 1a-1n to the cloud 54 or the local computer system 60. Data associated with the devices 1a-1n may be transferred to cloud-based computers via the router for remote data processing and manipulation. The operating theater devices 1a-1n may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
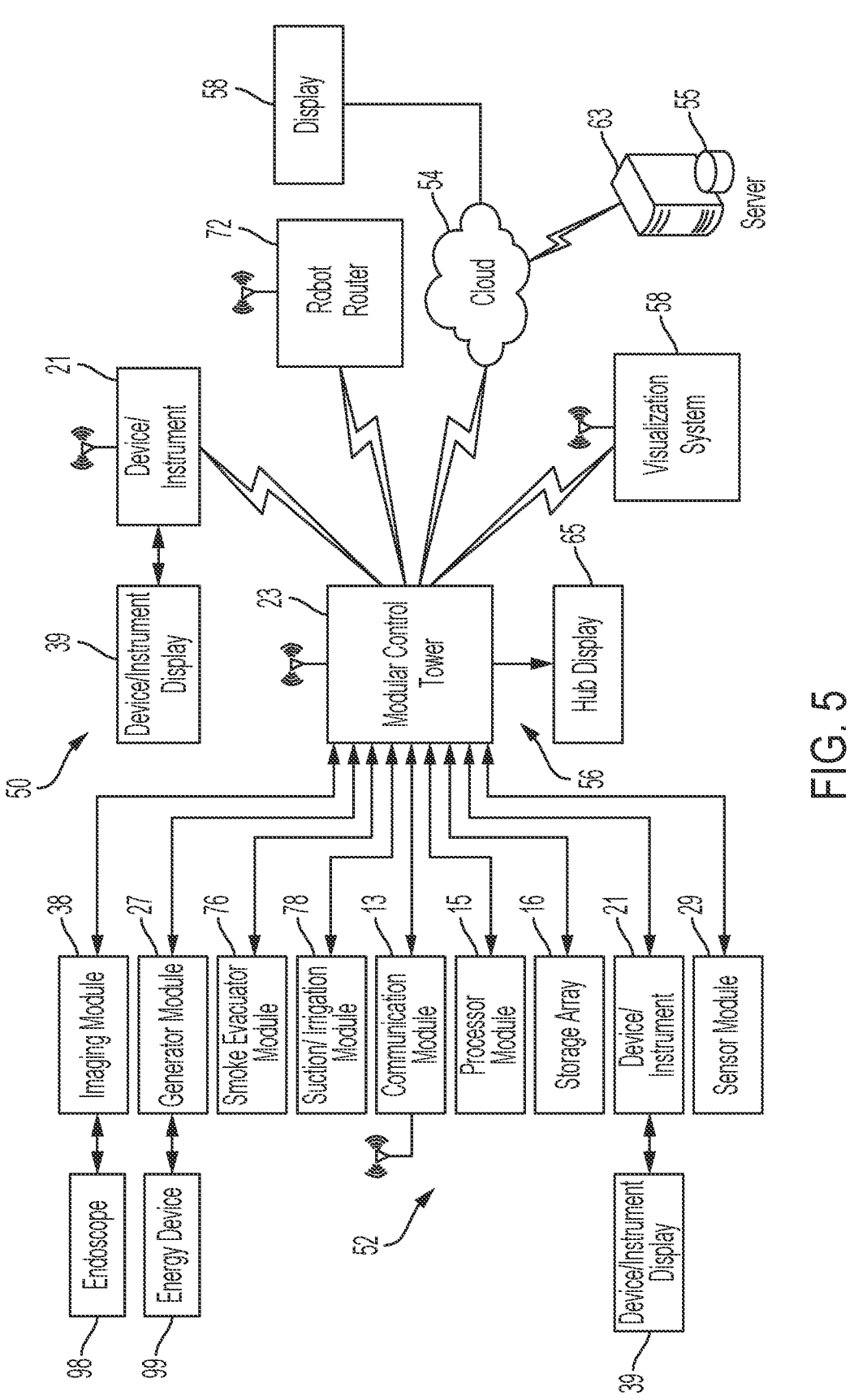
FIG. 5 illustrates a computer-implemented interactive surgical system, according to one aspect of this disclosure.
Figure 6:
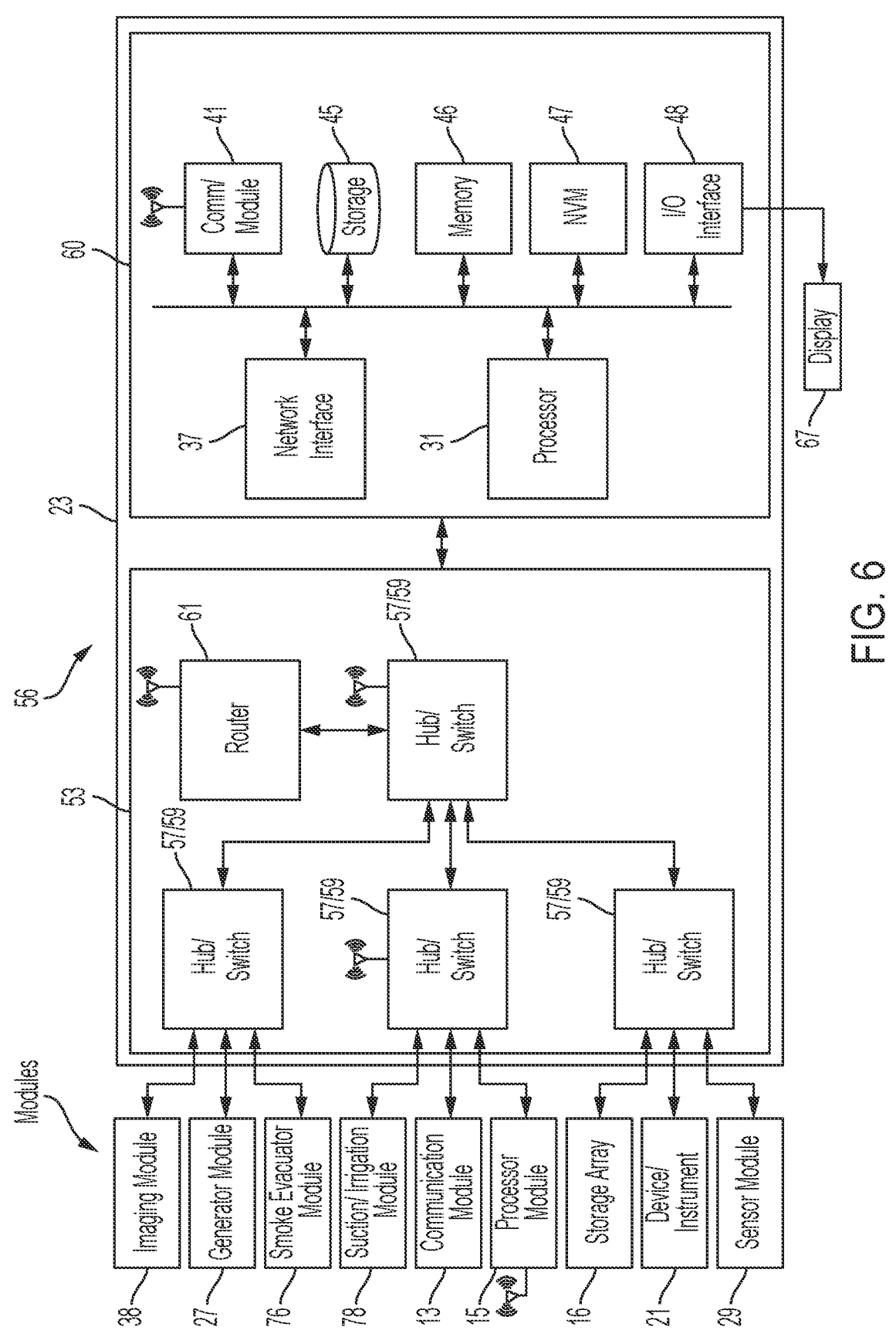
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics processing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

Figure 7:
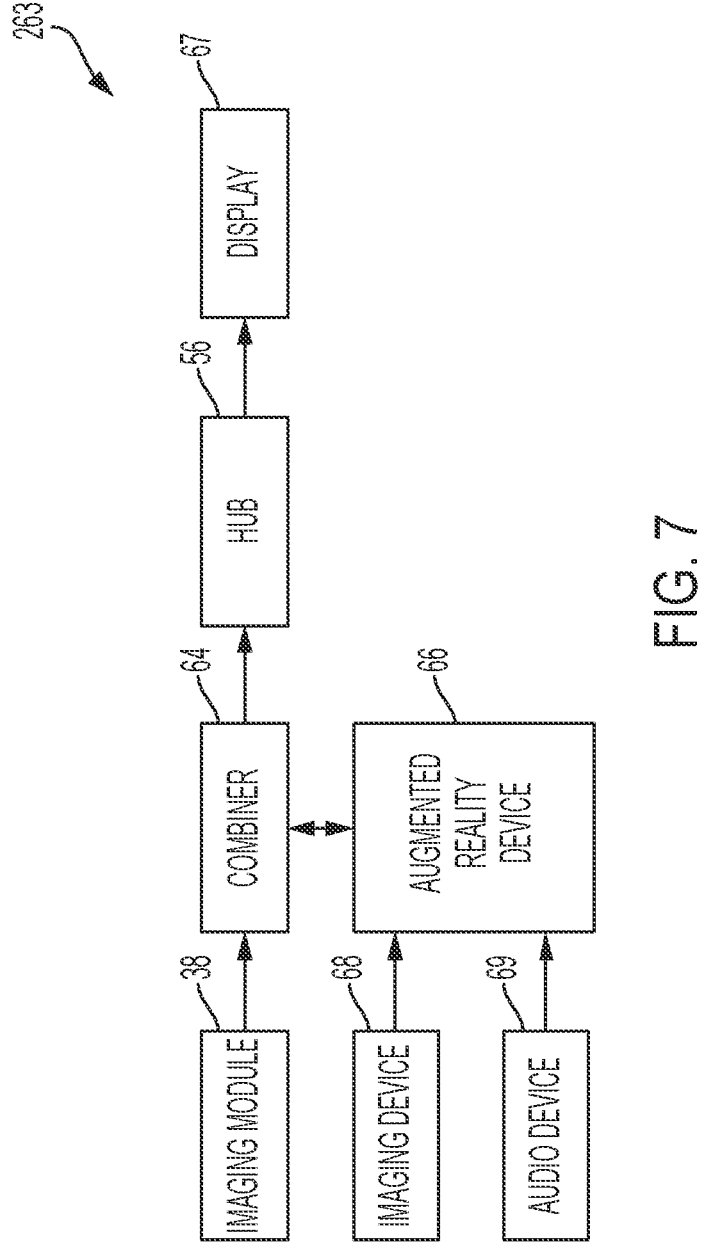
FIG. 7 illustrates an augmented (AR) reality system comprising an intermediate signal combiner positioned in the communication path between an imaging module and a surgical hub display, according to one aspect of this disclosure.

FIG. 7 illustrates an augmented reality system 263 comprising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
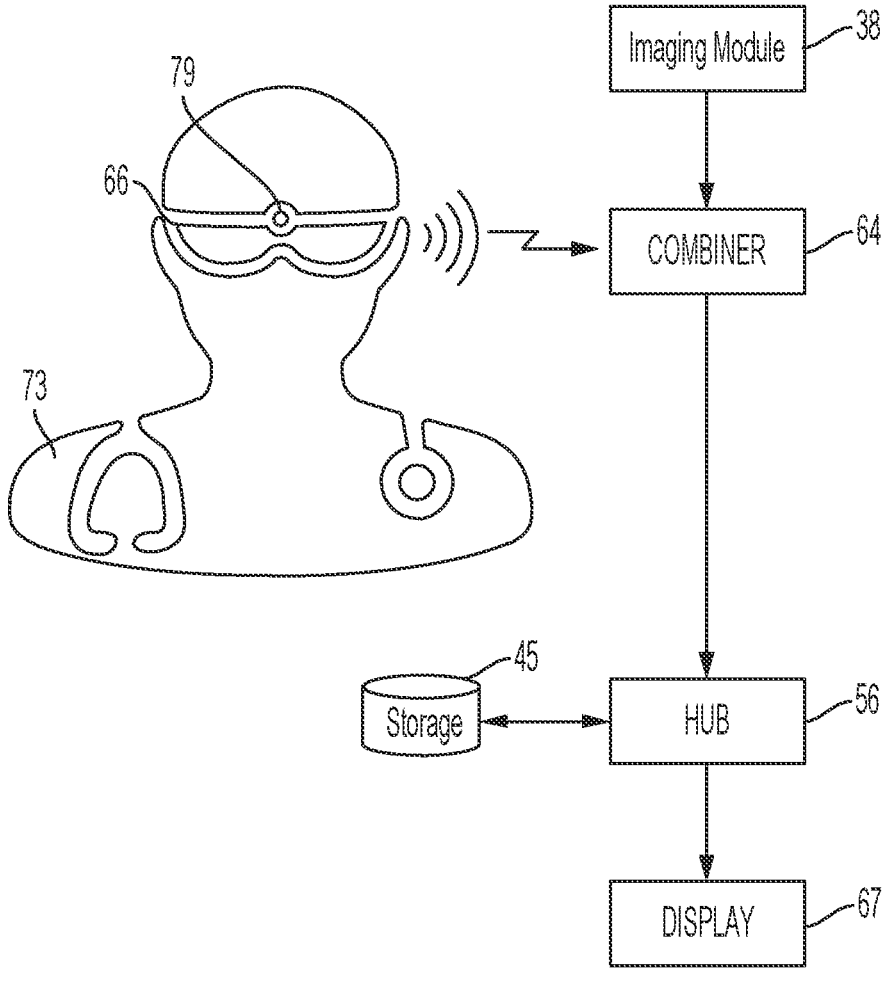
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure-ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
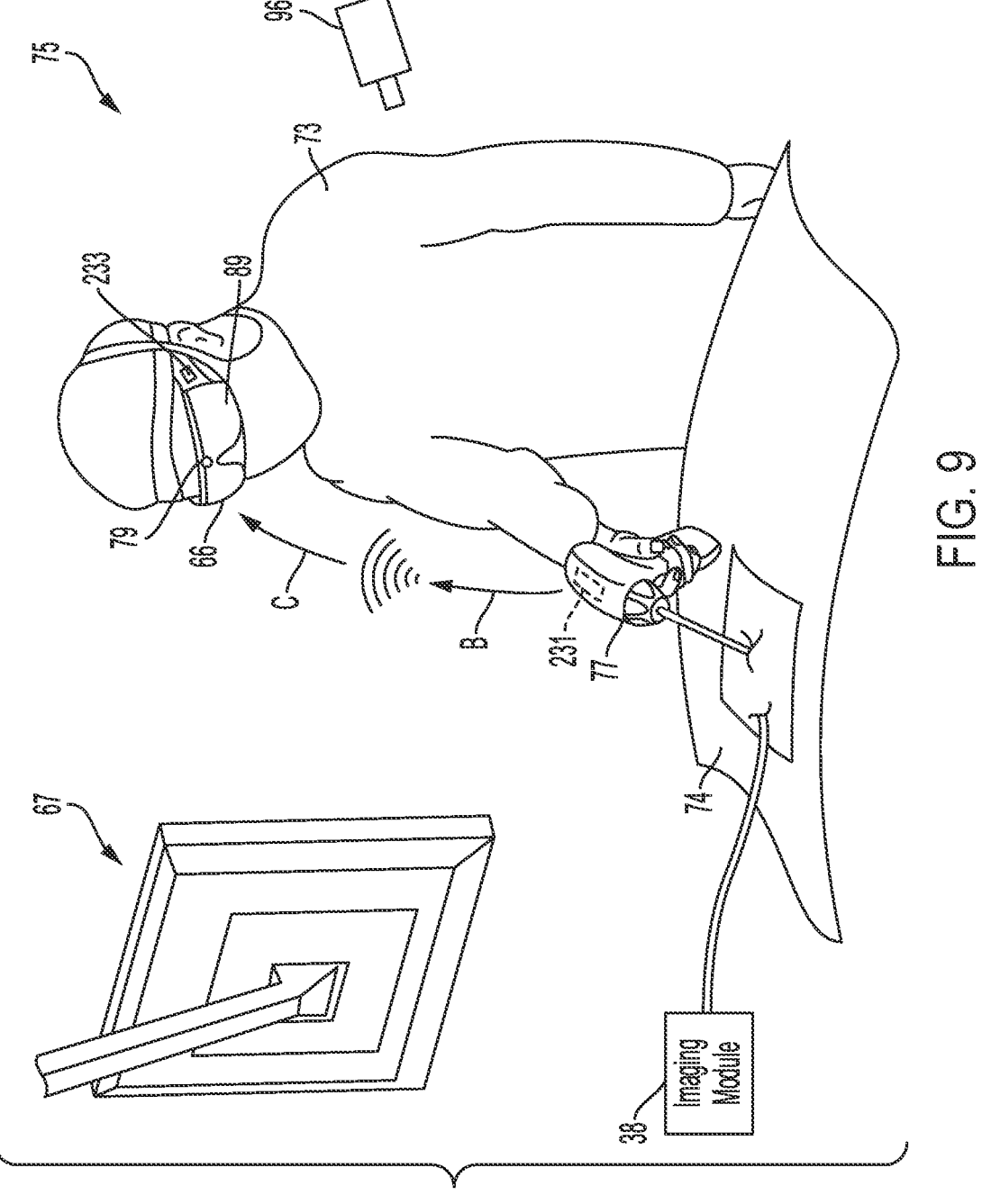
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see different virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, in accordance with at least one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a Hololens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step S212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step S224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step S202 of the timeline 5200 depicted in FIG. 11, the patient data can also be utilized by a situationally aware surgical hub 5104 to generate control adjustments for the paired modular devices 5102.

Mixing Directly Visualized with Rendered Elements to Display Blended Elements and Actions Happening On-Screen and Off-Screen Having described a general implementation of the various surgical systems, surgical hubs, communication systems, augmentation systems, and augmented reality devices disclosed herein, such as surgical systems 1, 2, 50, 52, surgical hubs 6, 56, 5104, communication system 63, visualization system 8, augmentation system 83, imaging devices 24, 96 and AR devices 66, 84, the disclosure now turns to describe various other implantations of the systems, hubs, and devices. For the sake of brevity, various details and implementations of the systems, hubs, and devices described in the following sections, which are similar to the various systems, hubs, and devices described above, are not repeated herein. Any aspect of the systems, hubs, and devices described below can be brought into and/or be implemented by the above systems, hubs, and devices.

As explained above, augmented reality display devices and other types of display devices can be used to provide overlays of information to operating room (OR) staff during a surgical procedure. In some aspects, these overlays can include information related to the step of a procedure that the OR staff member is performing. Thus, the information displayed by the overlay may need to be based on a surgical instrument that the staff member is using or an area of the surgical field that the staff member is working in. However, during a surgical procedure, there are often multiple OR staff members interacting with a wide variety of surgical instruments and other objects. Moreover, surgeons, nurses, and assistants may all be working in and around the surgical field at various times. Thus, each staff member may move throughout the operating room and handle multiple surgical instruments, passing instruments to each other and setting instruments aside when they are not in use. Given the constantly changing situation in the OR, it can be difficult for surgical systems to track and organize the information that needs to be displayed to various staff members on various devices throughout the surgical procedure. Accordingly, there is a need for apparatuses, systems, and methods for tracking multiple users and objects within the OR so that relevant information can be properly displayed by various augmented reality and other display devices.

Furthermore, at various times during a surgical procedure, staff members, instruments, and other objects may pass in and out of the view of various imaging devices of the surgical system, such as imaging devices configured to capture an image of the surgical field. As a result, staff members relying on augmented reality and other display devices that are displaying the captured images of the surgical field may not be able to view a portion of an instrument that is actively being used. Thus, the staff member may not be able to accurately perceive important attributes of the instrument. For example, a surgeon performing a transection using an endo-cutter may not be able to view a portion of the endo-cutter as it passes outside of the field of view of an endoscope. Because of the obstructed view, the surgeon may not be able to perceive the articulation range of the endo-cutter's end effector. Or, in another example, the surgeon may not be able to perceive the position of the end effector. Thus, the surgeon may have trouble accurately performing the transaction. Accordingly, there is a need for apparatuses, systems, and methods for tracking attributes of surgical instruments outside of the field of view of an imaging device and displaying the tracked attributes using overlays on augmented reality devices and other display devices.

Yet further, at various times during a surgical procedure, surgical instruments and other objects may be outside of the field of view of various imaging devices. Thus, staff members relying on augmented reality and other display devices may not be able to perceive potential interactions of the surgical instrument and other objects outside of the field of view. For example, a surgeon may be using an energy device for a step of a surgical procedure. However, viewing a display device showing a live image of the surgical field captured by an endoscope, the surgeon may not be able to perceive that the energy device is in close proximity to a metallic instrument outside the field of view of the endoscope. Accordingly, there is a risk that the surgeon could activate the energy device in close proximity to the metallic instrument, causing a malfunction of the energy device (e.g., electric arcing). As another example, a surgeon attempting to perform a procedure using a circular stapler may be able to view a device deck of the stapler that is within the field of view of the imaging device but not be able to view an anvil that it outside of the field of view. Thus, the surgeon may have difficulty routing and manipulating tissue to optimize the attachment of the device deck and anvil. As yet another example, a surgeon operating a device may not be able to perceive potential collisions or unintended interactions between a surgical instrument and an object that is outside of the field of view of the imaging device. Accordingly, there is a need for apparatuses, systems, and methods for predicting interactions of surgical instruments with objects that are outside of the field of view of imaging devices and displaying attributes of the surgical instruments related to the potential interactions.

Real-Time Location Tracking of Objects

In various aspects, apparatuses, systems, and methods for tracking multiple users and objects within the OR are disclosed herein. In some aspects, these apparatuses, systems and methods for tracking multiple users and objects can be employed to ensure that relevant information related to the tracked objects can be displayed to the specific user(s) using the various augmented reality and other display devices disclosed herein.

Figure 12:
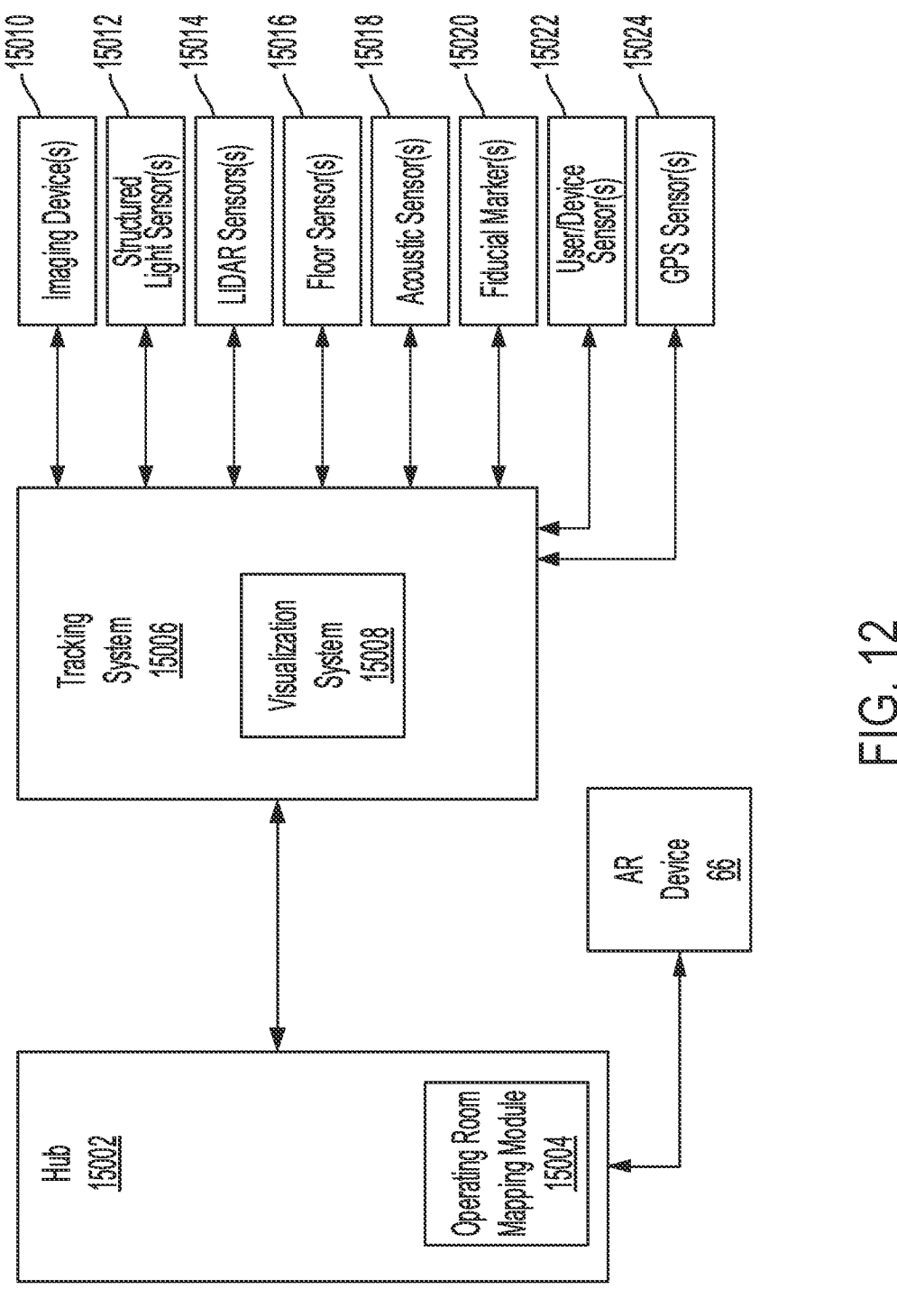
FIG. 12 illustrates a surgical system including a tracking system configured to track objects within an operating room, according to one aspect of this disclosure.

FIG. 12 depicts an example of a surgical system 15000 for tracking the location of objects within an OR, according to several non-limiting aspects of this disclosure. The surgical system 15000 can include a surgical hub 15002 in communication with a tracking system 15006 and at least one AR device 66. In some aspects, the tracking system 15006 can include a visualization system 15008. The surgical system 15000, surgical hub 15002, and visualization system 15008 can be similar in many aspects, respectively, to any of the surgical systems, surgical hubs, and visualization systems described above, (e.g., surgical systems 1, 2, 50, 52; surgical hub 6, 56, 5104; visualization systems 8, 58). In the non-limiting aspect of FIG. 12, the tracking system 15006 is in communication with the surgical hub 15002. In other aspects, the surgical hub can include a module comprising the tracking system 15006. The surgical hub 15002 can include an operating room mapping module 15004 configured to map the location and/or status of various objects within the OR based on data received from the tracking system 15006, as discussed in more detail below.

The tracking system 15006 can be configured to track the position and/or other attributes of various objects within the OR based on one or more different types of tracking methods. In one aspect, the tracking system 15006 (and/or the visualization system 15008) can include one or more imaging devices 15010. The imaging device(s) 15010 can be similar in many aspects to the imaging devices 24, 96, the AR device 66 and/or other imaging sensors described above with respect to visualization system 8. Thus, the imaging device(s) 15010 can include cameras and other types of visible and non-viable sensors for capturing images or otherwise tracking objects within the OR. For example, the imaging device(s) 15010 may employ visual, infrared, and/or other higher wavelength image recognition techniques to establish positional movements and locations of objects within the OR. Imaging device(s) 15010 may be placed in multiple locations throughout the operating room with over-lapping fields of view such that images of objects within the OR can be captured and tracked from multiple angles. Further, multiple imaging devices 15010 may be implemented such that an object in the OR can be tracked by at least a second imaging device 15010 (e.g., a second camera 15010) when the object leaves the field of view of a first imaging device 15010 (e.g., a first camera 15010).

In another aspect, the tracking system 15006 can include one or more structured light sensors 15012 (e.g., structured light scanners) configured to track objects in the OR. The structured light sensor(s) 15012 can be configured to project a defined pattern of light, for example, from multiple angles in order to triangulate the position of objects within the OR based on distortion of the pattern caused by the objects. The structured light sensor(s) 15012 may be similar to and/or include devices such as Microsoft Kinect, Intel F200, Intel R200, and or Occipital Structure.

In another aspect, the tracking system 15006 can include one or more LIDAR (Light Detection and Ranging) sensors 15014 configured to track objects in the OR. In other aspects, sensors that use techniques similar to LIDAR may be employed by the tracking system 15006 to track objects in the OR.

In another aspect, the tracking system 15006 can include one or more floor sensors 15016 configured to track objects in the OR. The floor sensors 15016 can include weight sensors. In one aspect, the tracking system can include an array of floor sensors 15016 that are configured to determine where equipment is placed within the OR. For example, referring now to FIGS. 2 and 12, the floor sensors 15016 can be configured to determine the location and/or position of the operating table 14, surgeon's console 18, robotic hub 22, side cart 20, etc. In another aspect, the floor sensors 15016 can be configured to monitor the location and/or position of staff members within the OR.

The data generated by the floor sensors 15006 may be processed by the surgical hub 15002 and to make determinations related to various aspects of a surgical procedure. For example, a weight measured by the floor sensors 15006 could be used to determine if a device has been placed on a side cart or other piece of OR equipment (e.g., by recognizing a change in weight when the device is placed). As another example, the floor sensors 15006 can be used to detect fatigue of the OR staff based on their movements (e.g., swaying, weight distribution, etc.). As another example, the floor sensors can be used to track the weight of a patient during surgery. The patient weight may be verified by the surgical hub 15002 throughout a procedure for various reasons, such as to ensure that the dose of a drug administered to the patient is within an acceptable range for that patient's weight, as tracked by the tracking system 15006. As yet another example, the floor sensors 15016 can be used to track medical waste, devices, equipment, etc. that fall to the floor during a procedure.

Referring still to FIG. 12, in another aspect, the tracking system 15006 can include one or more acoustic sensors 15018 configured to monitor the position, location, and/or movement of objects in the OR. For example, the acoustic sensors 15018 may employ audio beaconing techniques, phase-coherent tracking, and/or time-of-flight triangulation to establish the positional movement of an object in the OR.

In another aspect, the tracking system 15006 can include one or more fiducial markers 15020. In one aspect, the fiducial markers 15020 can be any type of marker configured to assist in tracking the location, position, and/or movement of an object relative to the field of view of the imaging device(s) 15010 and/or relative to location, position and/or movement data tracked by any of the other devices/sensors of the tracking system 15006. For example, the fiducial marker(s) 15020 can include an RFID (radio frequency identification) chip configured to track the location and/or position of an object that the RFID chip is attached to. Thus, in some aspects, the fiducial markers(s) 15020 can be placed in and/or on a surgical device, operating room equipment, objects worn by OR staff, or any other object that may be tracked by the tracking system 15006. In some aspects, tracking of the fiducial markers 15020 by the tracking system 15006 can be triggered to start based on the occurrence of an event such as, for example, removal of an object (e.g., device) comprising the fiducial marker 15020 from its packaging, inserting a battery into an object (e.g., device) comprising the fiducial marker 15020, and/or when an object comprising the fiducial marker 15020 enters the OR. The fiducial markers 15020 can be used to assist in the generation of augmented reality overlays, as discussed in more detail below.

In another aspect, the tracking system 15006 can include one or more user/device sensors 15022 configured to identify and monitor the position, location, and/or movement of OR staff and/or devices within the OR. In one aspect, the user/device sensors 15022 can be included in devices or equipment worn by OR staff. The user/device sensors 15022 can include, for example, accelerometers, gyroscopes, and/or magnetometers to track the three-dimensional movements of OR staff and/or devices. In other aspects, user/device sensors 15022 can include, an RFID bracelet worn by OR staff. In one aspect, data from the user/device sensors 15022 can be used by the surgical hub 15002 and/or the tracking system 15006 to associate a device (e.g., surgical instrument) to a specific user within the OR at a given time during the surgical procedure. For example, the tracking system 15006 and/or the surgical hub 15002 may be configured to separately track the movements of OR staff and devices using multiple user/device sensors 15022. When the tracking system 15006 detects that a user/device sensor 15022 worn by an OR staff member is proximate to a user/device sensor 15022 associated with a surgical instrument, the surgical hub 15006 can identify that the OR staff member is associated (e.g., linked, using) the surgical instrument. Based on the identified association of the staff member and the instrument, the surgical hub 15002 can cause the generation of augmented reality overlays specific to the staff member and/or surgical instrument, as explained in more detail below with respect to FIGS. 12-14. In another aspect, the user/device sensors 15022 can be used to identify instruments and/or devices. The user/device sensors 15022 may include RFID tags to identify the specific type of device that is being used during a procedure. As one example, the user/device sensor 15022 can be an RFID tag on a trocar to identify the kind of trocar being used.

In another aspect, the tracking system 15006 can include one or more GPS (global positioning system) sensors 15024 that are tracked using GPS (e.g., satellite) tracking techniques to monitor the position, location, and/or movement of objects in the OR. It should be noted that although the tracking system 15006 of FIG. 12 is shown implementing tracking techniques including imaging device(s) 15010, structured light sensor(s) 15012, LIDAR sensor(s) 15014, floor sensor(s) 15016, acoustic sensor(s) 15018, fiducial marker(s) 15020, user/device sensor(s) 15022, and GPS 15024, the tracking system 15006 can be configured to use any combination of these techniques (e.g., including only some of these techniques). Further, in some aspects, other tracking techniques configured to track the location, position, movements, and/or other attributes of objects in the OR may be implemented by the tracking system 15006.

Figures 13, 14:
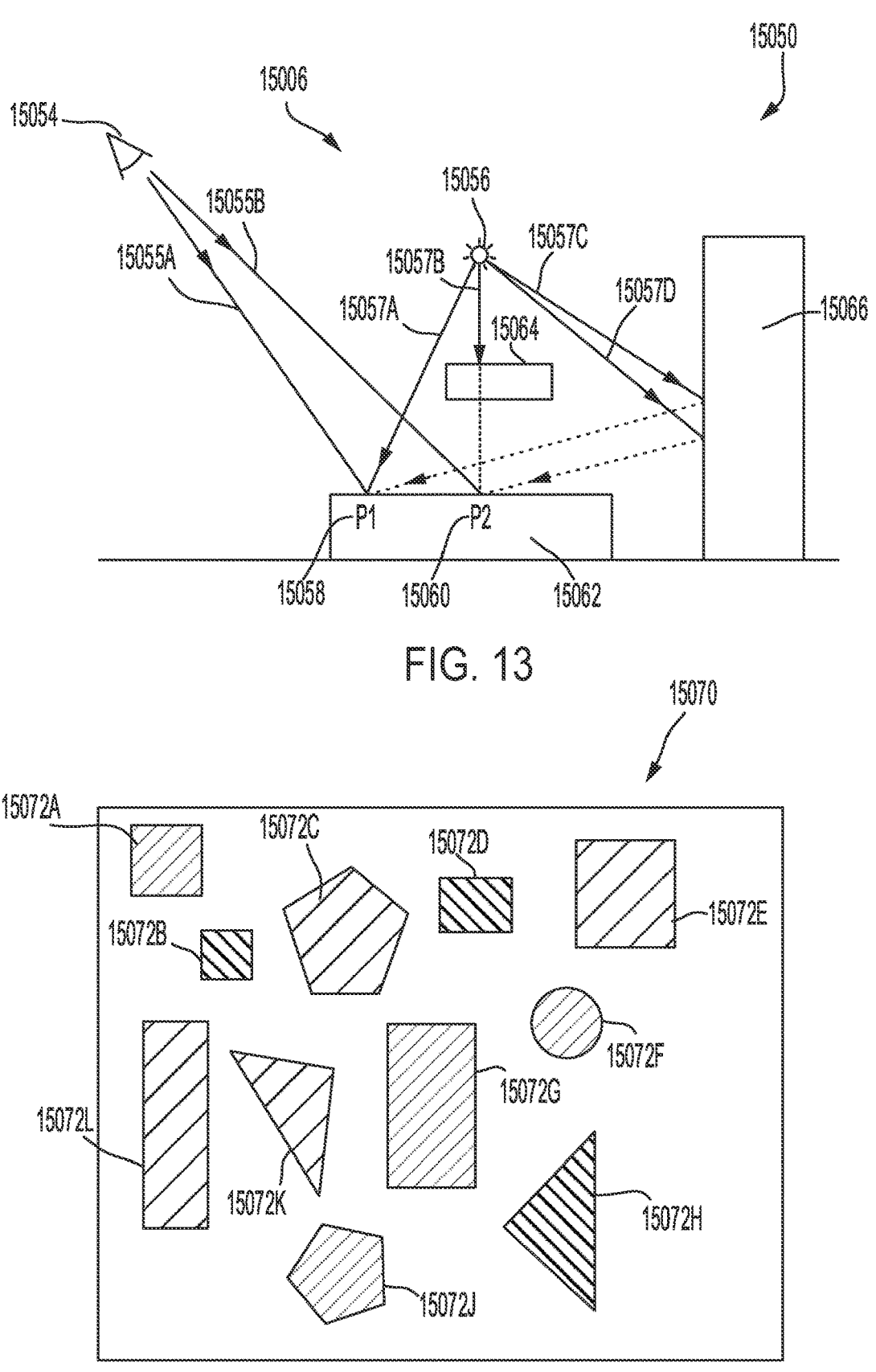
FIG. 13 illustrates a schematic side view of an exemplary implementation the tracking system of FIG. 12 in an operating room, according to one aspect of this disclosure.
FIG. 14 illustrates a schematic plan view of an exemplary operating room map generated by an operating room mapping module, according to one aspect of this disclosure.

FIG. 13 illustrates a schematic side view of an exemplary implementation the tracking system 15006 in an operating room (OR) 15050, according to several non-limiting aspects of this disclosure. The OR 15050 can be any portion of an OR. For example, in some aspects, FIG. 13 can illustrate an overall side view of an OR 15050. In other aspects, FIG. 13 can illustrate a cross-sectional side view of a surgical field. The tracking system 15006 can include a first tracking device 15054 and a second tracking device 15056. The first tracking device 15056 and/or the second tracking device 15054 may be implemented using any combination of the tracking techniques referenced above with respect to FIG. 12 (e.g., imaging device(s) 15010, structured light sensor(s) 15012, LIDAR sensor(s) 15014, acoustic sensor(s) 15018, etc.). The first tracking device 15056 and the second tracking device 15054 may implement the same tracking technique or a different tracking technique.

Referring primarily to FIG. 13, and also to FIG. 12, in some aspects, the first tracking device 15054 and/or the second tracking device 15056 can be configured to track a first portion 15058 and a second portion 15060 of a target object 15062. The target object 15062 may be and object or area such as, for example, an object within the surgical field, an area within a sterile barrier, a patient, tissue, OR equipment, a surgical device, OR staff, etc. The first tracking device 15054 may be able to directly track 15055A, 15055B the first portion 15058 and the second portion 15060 of the target object 15062. For example the first tracking device 15054 may be a camera (e.g., imaging device 15010) with the first portion 15058 and the second portion 15060 of the target object 15062 directly 15055A, 15055B in a field of view of the camera. The second tracking device 15056 may be able to directly track 15057A the first portion 15058 of the target object 15062. However, the second tracking device 15056 may not be able to track 15057B the second portion 15060. For example, the second tracking device may be a camera (e.g., imaging device 15010) and the second portion 15060 may be outside of the field of view of the camera. This may be because an obstructing object 15064 (e.g., an OR staff member, a surgical instrument, tissue, etc.) is blocking the tracking 15057B of the second portion 15060 of the target object 15062. Despite the obstructing object 15064 blocking the tracking 15057B of the second portion 15060 of the target object 15062 by the second tracking device 15056, the tracking system 15006 can still track the second portion 15060 because the first tracking device 15054 is directly tracking 15055B the second portion 15060. Thus, the tracking system 15060 can be configured to have tracking devices tracking overlapping tracking areas (e.g., multiple imaging devices/systems with overlapping fields of view) so that target objects can be tracked when the target object or a portion of the target object is outside of the field of view of one of the tracking devices. Accordingly, the surgical hub 15002 is able to cause display devices to display information (e.g., images, overlays, notifications, etc.) related to the target object even when the target object or a portion thereof is outside of the field of view of one of the tracking devices.

Still referring primarily to FIG. 13, and also to FIG. 12, in other aspects, the first tracking device 15054 and/or the second tracking device 15056 may include a tracking device that is configured to directly 15055A, 15055B, 15057A and/or indirectly track 15057C, 15057D the first portion 15058 and the second portion 15060 of the target object 15062. For example, the second tracking device 15056 may be a device that implements a reflective tracking technique (e.g., an acoustic sensor(s) 15018) such that when an obstructing object 15064 prohibits direct tracking 15057B, the second tracking device 15056 can indirectly track 15057C, 15057D the target object 15062 (e.g., based on reflection using an object 15066). Thus, the tracking system 15060 can be configured to have tracking devices with overlapping tracking areas (e.g., including areas tracked using non-image techniques, reflective techniques, audio beaconing, GPS, RFID, etc.) to track the location, position, movement, and/or other attributes of a target object.

FIG. 14 illustrates a schematic plan view of an exemplary operating room map 15070 generated by the operating room mapping module 15004 of FIG. 12, according to at least one non-limiting aspect of the present disclosure. Referring primarily to FIG. 14, and also to FIGS. 12-15, the tracking system 15006 can transmit tracking data to an operating room mapping module 15004 of surgical hub 15002 generated using any combination of tracking techniques (e.g., imaging device(s) 15010, structured light sensor(s) 15012, LIDAR sensor(s) 15014, floor sensor(s) 15016, acoustic sensor(s) 15018, fiducial marker(s) 15020, user/device sensor(s) 15022, and GPS 15024). Based on the tracking data, the operating room mapping module 15004 can generate an operating room map 15070 of an operating room 15060. The map 15070 can include information related to the location, position, motion, and/or other attributes of multiple objects (e.g., 15072A-15072L) within the operating room 15060. For example, the objects 15072A-15072L of the map 15070 can correspond to various devices, equipment, OR staff, present in the operating room. The map 15070 can be updated in real-time based on tracking data from the tracking system 15006. In some aspects, the map 15070 may be displayed by any of the display devices disclosed herein. In other aspects, the surgical hub 15002 can determine the proximity and/or interaction of objects based on the map 15070.

Multi-User Track and Information Association

Referring to FIG. 12-14, in other aspects, augmented reality overlays and other notifications and alerts can be generated based on the location, position, and/or motion of objects (e.g., 15072A-15072L) as determined by the operating room mapping module 15004. In some aspects, users and devices can be tracked using the tracking system 15006 both based on the user/device sensors 15022 and other sensing techniques (e.g., imaging device(s) 15010, structured light sensor(s) 15012, LIDAR sensor(s) 15014, floor sensor(s) 15016, acoustic sensor(s) 15018, GPS 15024, etc.). In some aspects, as mentioned above, user and device sensor data can be used by the surgical hub 15002 (e.g., the operating room mapping module 15004) and/or the tracking system 15006 to associate a device (e.g., surgical instrument) to a specific user within the OR at a given time during the surgical procedure. In this aspect, both active (wearables) and passive (cameras) tracking methods can be used by the tracking system 15006 and the operating room mapping module 15004 to map 15070 the location of devices and staff within the OR suite. For example, users (surgeons and OR other staff members) may wear gloves including user/device sensors 15022. In one aspect, the surgical hub 15002 can be configured to identify the gloves as linked to a user's right and left hands.

In some aspects, the operating room mapping module 15004 can be configured to associate users with specific locations within the operating room map 15070. For example, the operating room map 15070 may divide the OR 15060 into specific areas. Based on data from the tracking system 15006, the operating room mapping module 15004 can identify the user who has prioritization and/or control over a device. As a user exchanges a device (e.g., transfers physical control over a device to a different user), sensors (e.g., device/user sensors 15022) can detect the exchange, thereby enabling the surgical hub 15002 to identify which user is associated with the device. For example, gloves worn by the users may be configured with sensors tracking finger pressure and position. The surgical hub 15002 (e.g., the operating room mapping module 15004) can determine which has control over a device based on the glove sensor data, device sensor data, and/or data from imaging devices 15010 to calculate likelihoods of who is directing the device.

In various aspects, the surgical hub 15002 can cause any of the display and/or AR devices described herein (displays 7, 9, 19; AR devices 66, 84) to display notifications, alerts, and/or overlays based on data from the tracking system 15006, operating room mapping module 15004, and/or the surgical hub 15002. In one aspect, notifications can be displayed to one or more users based a determination by the operating room mapping module 15004 that a user has control over a surgical instrument. For example, an AR device that a surgeon is wearing can display a notification indicating that the surgeon has taken control over a surgical instrument handed to the surgeon by another OR staff member. As another example, both a first AR device that the surgeon is wearing and a second a AR device that the OR staff member is wearing can display the notification indicating that the surgeon has taken control over the surgical instrument from the OR staff member. In some aspects, whether or not a particular user's AR device displays a notification can be based on a priority level related to the data tracked by the tracking system 15006 and/or information determined by the surgical hub 15002.

In one aspect, a surgical device may be intended to be used by multiple users simultaneously. In this aspect, portions (e.g., sections) of the surgical device can be individually tracked by the tracking system 15006. For example, a circular stapling device can include device portion with a retractable trocar controllable by an adjustable knob. The circular stapling device can also include an attachable an anvil portion. The different portions of the circular staple device can be controlled by different users and separately tracked by the tracking system 15006. Based on data from the tracking system 15006, display devices (e.g., AR devices) associated with each user can be configured to display different overlays based the portion(s) of the device the user has control over. For example, a display associated with the user controlling the adjustable trocar can display an overlay based on the dialing pressure as the user adjusts the knob. The displays associated with both users may display a status of the anvil being attach to the trocar.

In some aspects, users may not be wearing a trackable sensor (e.g., user/device sensor 15022). The tracking system 15006 can be configured to track actions of the user and/or devices controlled by the user using passive tracking (e.g., using an imaging device 15010). For example, a nurse may not be wearing a trackable sensor. The nurse may perform reload of an endo-cutter with a staple cartridge. Specific cartridge types may be color coded. The reload exchange performed by the nurse can be detected based on a camera of the tracking system. Further, a notification based on the reload exchange detected by the camera can be displayed to the user who the surgical hub 15002 determined as last using the device (e.g., a surgeon wearing an active tracking device). The notification can include an overlay indicating the type of cartridge that was reloaded based on the color of the cartridge detected by the camera of the tracking system 15006. This tracking can enable the detection of potential mistakes, such as the loading of an incorrect type of staple cartridge into the endo-cutter. This tracking can also enable the issuance of warnings (e.g., display notifications) based on these detections. Further, this tracking can provide users with an awareness of actions that the users cannot directly observe.

FIG. 15 is a table 15100 of exemplary tracked object interactions determined by the surgical hub 15002 based on data generated by the tracking system 15006, according to at least one non-limiting aspect of the present disclosure. Each tracked object interaction 15102 is associated with a timestamp 15104 and a position 15106 of the object(s) during the interaction. Where applicable, the object interaction is associated with a glove ID 15108 and device ID 15110 based on the user and/or device involved in the object interaction (e.g., as determined based on user/device sensors 15022, imaging devices 15010, etc.). In cases where multiple portions of the device are tracked, the object interaction also includes a device portion identifier 15112. The table also includes a type of action 15114 that is determined by the surgical hub 15002 based on the tracked information associated with the object interaction(s). The table also includes the tracking source 15116 (e.g., imaging device(s) 15010 (cameras); user/device sensors 15022 (wearable)). Thus, based on data from the tracking system 15006, the surgical hub 15006 is able to identify various actions occurring during a surgical procedure, such as device handoffs, device operations, etc.

In various aspects, the information shown in the exemplary table of FIG. 15 can be stored in a non-relational database or in formats such as JSON arrays, thereby allowing additional information to be associate with an entry (e.g., stored by storage device 5 of FIG. 1; storage device 55 of FIG. 5, etc.). For example, detected object interactions may be entered into an even log comprising a variety of device-related information such as the timestamp, device position/rotation, equipment/device ID, and the determined action. In some aspects, the information can be associated with device-sensed data such as tracked forces/stresses, finger positions, and other relevant diagnostic data.

Off-Screen Interaction with Rendered Imagine that are Created Based on Predictions In various aspects, apparatuses, systems, and methods for tracking attributes of surgical instruments outside of the field of view of an imaging device and displaying the tracked attributes using overlays on augmented reality devices and other display devices are disclosed herein. Referring again to FIG. 12, the surgical system 15000 can include a tracking system 15006 configured to visualize and/or track various objects within the operating room. As explained above, in some aspects, the tracking system 15006 can include a visualization system 15008 and one or more imaging devices 15010. The visualization system 15008 can be similar in many aspects to visualization systems 8, 58 described herein and the imaging device(s) 15010 can be similar in many aspects to the imaging devices 24, 96, the AR device 66 and/or other imaging sensors described herein. Thus, the visualization system 15008 can be configured to capture images (e.g., a live feed) of the surgical field during a surgical procedure. For example, the visualization system can capture an image of a surgical instrument in the surgical field as the surgical instrument is used to perform a step of a surgical procedure. The images captured by the visualization system 15008 can be displayed by any of the display devices disclosed herein, such as augmented reality (AR) display devices, to assist surgical staff during the surgical procedure.

As also explained above, in some aspects, the tracking system 15006 can utilize fiducial marker(s) 15020 to track various attributes of surgical devices. The fiducial markers 15020 can be any type of marker configured to assist in tracking the location, position, and/or movement of an object relative to the field of view of the imaging device(s) 15010 and/or relative to the location, position, and/or movements detected by other sensors/devices of the tracking system 15006. For example, the fiducial marker(s) 15020 can include an RFID (radio frequency identification) chip configured to track the location and/or position of an object that the RFID chip is attached to. Thus, in some aspects, the fiducial markers(s) 15020 can be placed in and/or on a surgical device, operating room equipment, objects worn by OR staff, or any other object that may be tracked by the tracking system 15006.

In various aspects, the surgical hub 15002 can be configured to cause a display of the surgical system 15000 (e.g., AR device 66) to display a captured image of an object in a surgical field based on the imaging device(s) 15010 overlaid with a graphic representing an attribute of the object determined based on the fiducial marker(s) 15020. In some aspects, the fiducial marker 15020 could be included on/in a surgical instrument. Based on the fiducial marker(s), the tracking system 15006 can be configured to identify the type of surgical instrument that is associated with the fiducial marker(s) 15020 and/or various other attributes of the surgical instrument.

In one aspect, the tracking system 15006 can detect a position and orientation of a fiducial marker 15020. The fiducial marker may be located on a first portion of the surgical instrument. Based on the detected position and orientation of the fiducial marker 15020, the surgical hub 15002 can determine the position and orientation of a second portion of the surgical instrument relative to the image of the surgical field captured by an imaging device 15010. Thus, the surgical hub 15002 can cause the AR device 66 to display a graphic related to the position and orientation of the second portion of the surgical instrument, overlaid on an image of the surgical field, based the fiducial marker 15020. In another aspect, the second portion of the surgical instrument may be outside of the field of view of the imaging device 15010. Therefore, the second portion of the surgical instrument cannot be observed based only on the image captured by the imaging device 15010. In this aspect, the graphic related to the second portion of the surgical instrument can be displayed by the AR device 66 as an overlay on representing the position and orientation of the second portion of the surgical instrument. Thus, a user viewing the AR device 66 can perceive the position and orientation of the second portion of the surgical instrument even when this portion of the surgical instrument is outside of the field of view of the imaging device 15010.

For example, an endo-cutter may include a fiducial marker 15020 on a handle of the endo-cutter. Based on the fiducial marker 15020, the surgical hub 15002 can determine a position of the end effector or the endo-cutter. A surgeon using the AR device 66 to view an image of the surgical field captured by an imaging device 15010 surgeon may be operating the endo-cutter. The end effector may not be within the field of view of the imaging device 15010. Therefore, to assist the surgeon in perceiving the position and orientation of the end effector, the AR device 66 can display a graphic related to the position and orientation of the end effector. This graphic can be, for example, a rendered image of the end effector or a graphic object that points to the position of the end effector.

In some aspects, the tracking system 15006 and/or the surgical hub 15002 can determine various other attributes of an object based on the fiducial marker 15020. In one aspect, the fiducial marker 15020 can be associated with a surgical instrument having defined range of motion (e.g., defined volume and/or area of operation, articulation range, rotational range, etc.). Therefore, based on the fiducial marker 15020, the surgical hub 15002 can determine the range of motion of the instrument relative to an image of the surgical field. For example, the endo-cutter referenced in the paragraph above can have an articulation range of motion and/or rotational range of motion. Thus, based on tracking of the fiducial marker 15020, the surgical hub 15002 can demine the range of motion of the endo-cutter and display an overlay graphic representing the determined range of motion relative to the image of the surgical field.

In some aspects, the tracking system 15006 and/or the surgical hub 15002 can use fiducial markers 15020 to verify the identity of an object, such as the identity and/or type of a surgical instrument. For example, as explained above, surgical instruments may be communicatively connected to the surgical hub (e.g., device/instrument 21 and surgical hub 56 of FIG. 5). Based on this connection, the surgical hub can be configured to identify the instrument. The identification can include the type of instrument (e.g., a 45 mm stapler, a 60 mm stapler, etc.). Thus, the tracking system 15006 and fiducial marker 15020 may be used as an alternate and/or redundant means of identifying the surgical instrument. In one aspect, identifying the instrument based on the fiducial marker 15020 can include determining if the instrument is active and/or available for use.

In some aspects, the tracking system 15006 and/or the surgical hub 15002 can use fiducial markers 15020 as markers within the OR to provide a zero reference point. In another aspect, fiducial markers 15020 may be positioned at various locations around the OR to provide a frame of reference that may be used by the tracking system 15006 and/or surgical hub 15002 to orient other objects tracked by the tracking system 15006. For example, fiducial markers 15020 can be placed on patients and/or instruments to determine the relative location of the patient and instruments to each other. As another example, fiducial markers 15020 can be placed on instruments to determine the proximity and/or relative distance of the instruments to each other. As yet another example, fiducial markers 15020 can be placed on instruments and other equipment within the operating room, such as a table or cart, to demine if the instrument has been placed on the table.

In some aspects, the tracking system 15006 and/or the surgical hub 15002 can use fiducial markers 15020 to detect potential accidents and/or safety concerns related to the movement of an object. The detected potential accidents and/or safety concerns could be displayed as notifications via an AR overlay. In one aspect, fiducial markers 15020 can be positioned at various potions to designate a zero reference point and/or safety zone. The tracking system 15006 can be configured to detect when an object is approaching the safety zone or when an object is outside of the safety zone. For example, a surgical procedure may involve the use of a robotic system in conjunction with a laparoscopic instrument. Fiducial markers 15020 can be positioned to designate a safety zone within which the robotic system can safely maneuver the laparoscopic instrument. The tracking system 15006 and/or surgical hub 15002 can be configured to identify that the laparoscopic instrument is outside of the safety zone and provide a warning to the user and/or adjust the operation of the robotic system.

Figures 16A, 16B:
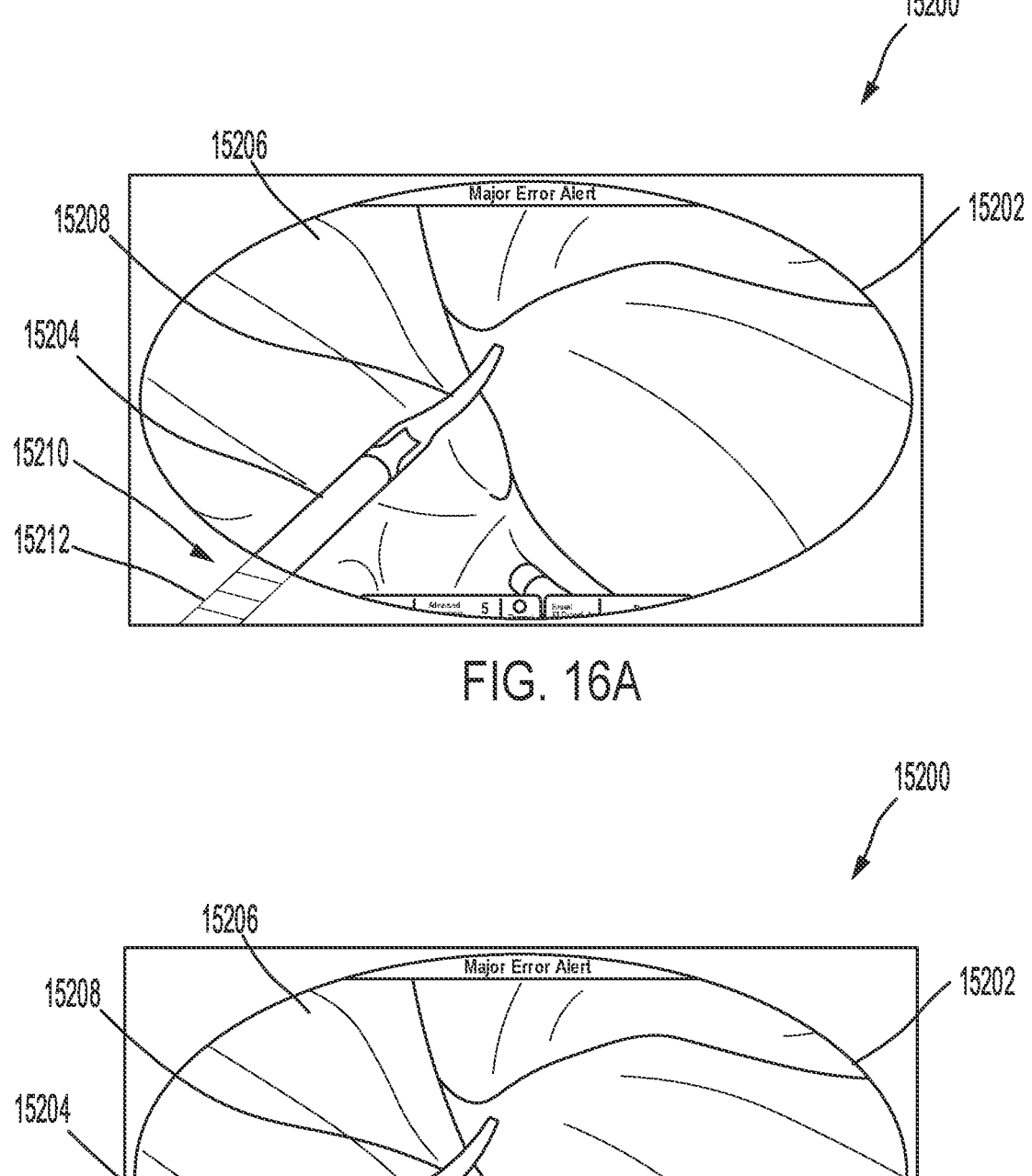
FIGS. 16A and 16B illustrate exemplary intraoperative displays including an image of a surgical instrument in a surgical field and a graphic representing a portion of the surgical instrument outside of the field of view, according to one aspect of this disclosure.

FIGS. 16A and 16B illustrate exemplary intraoperative displays 15200 including an image of a surgical instrument 15204 in a surgical field 15202 and a graphic 15212, 15214 representing a portion 15210 of the surgical instrument 15204 outside of the field of view, according to at least one non-limiting aspect of the present disclosure. The intraoperative displays 15002 can be displayed by any of the display devices (e.g., AR device 66) disclosed herein. Referring primarily to FIGS. 16A and 16B and also to FIG. 12, the image of the surgical field 15202 can be captured by an imaging device 15010. Based on the image of the surgical field 15202 captured by the imaging device 15010, a first portion 15208 of the surgical instrument 15204 (e.g., a grasper portion) can be seen interacting with tissue 15206. However, a second portion 15210 of the surgical instrument 15204 (e.g., a shaft portion) is outside of the field of view of the imaging device 15010 and therefore cannot be seen in the image of the surgical field 15202. The surgical instrument 15204 can include a fiducial marker 15020 (not shown in FIGS. 16A and 16B). Based on the fiducial marker 15020, the tracking system 15006 and/or the surgical hub 15002 can determine a position of the second portion 15210 of the surgical instrument 15204 relative to the surgical field. Thus, the surgical hub 15002 can cause the intraoperative display 15200 to include a graphic 15212, 15214 representing the position of the second portion 15210. In the non-limiting aspect of FIG. 16A, the graphic 15212 is a rendered image 15212 of the second portion 15210 of the surgical instrument

15204. In the non-limiting aspect of FIG. 16B, the graphic 15214 is a graphical object representing the position of the second portion 15210 of the surgical instrument 15204 relative to the image of the surgical field 15202.

Accordingly, the surgical system 15000 can track attributes of surgical instruments and display the tracked attributes using overlays displayed by AR display devices (e.g., AR device 66) and other display devices disclosed here. OR staff members may be relying on augmented reality and other display devices displaying the images of the surgical field captured by imaging devices. Surgical system 15000 can enable staff members to perceive portions of surgical instruments that may be outside of the field of view of the imaging devices. Moreover, surgical system 15000 can allow OR staff members to more accurately perceive important attributes of the instrument that may not be viewable based on a single imaging device, such as a range of motion of the instrument and/or the position of the instrument relative to other tracked objects.

Prediction of Interactions and Interrelationships of Objects not in the Field of View In various aspects, apparatuses, systems, and methods for predicting interactions of objects that are outside of the field of view of imaging devices and displaying attributes of the object based on the predicted interactions are disclosed herein. Referring again to FIG. 12, the surgical system 15000 can include a tracking system 15006 configured to visualize and/or track various objects within the operating room. As explained above, in some aspects, the tracking system 15006 can include a visualization system 15008 and one or more imaging devices 15010. The visualization system 15008 can be similar in many aspects to visualization systems 8, 58 described above and the imaging device(s) 15010 can be similar in many aspects to the imaging devices 24, 96, the AR device 66 and/or other imaging sensors described above. Thus, the visualization system 15008 can be configured to capture images (e.g., a live feed) of the surgical field during a surgical procedure. For example, the visualization system can capture an image of a surgical instrument in the surgical field as the surgical instrument is performing a step of a surgical procedure. The images captured by the visualization system 15008 can be displayed by any of the display devices disclosed herein, such as augmented reality (AR) display devices, to assist surgical staff during the surgical procedure.

In some aspects, as explained above, surgical instruments may be communicatively connected to the surgical hub (e.g., device/instrument 21 can be connected to surgical hub 56 of FIG. 5). Thus, the surgical hub 15002 can be configured to receive instrument data from surgical instruments related to various sensed parameters and operational settings of the instruments. Based on the instrument data received by the surgical hub 15002, the surgical hub 15002 can determine operating parameters of the instrument. For example, based on instrument data received from the various surgical instruments disclosed herein, the surgical hub 15002 can determine operating parameters such as to speed, force, firing speed, firing force, activation status, power level, activation time, energy mode, etc.

In some aspects, the surgical hub 15002 can be configured to identify interactions and potential interactions of surgical instruments and other objects based on data from the tracking system 15006 and/or based on instrument data received from the surgical instruments. Moreover, the potential interactions of the surgical instrument and the other object(s) may not be perceivable based only on images captures by an imaging device 15010 of the visualization system 15008. Therefore, a user relying on a display device (e.g., AR device 66) displaying only captured images from an imaging device 15010 may not be able to accurately respond to the potential interaction. Therefore, to assist the user, the surgical hub 15002 can be configured to cause the display device to display various notifications and other graphical indicators (e.g., overlays) related to the interactions and/or potential interactions detected by the surgical hub.

In one aspect, based on data from the tracking system 15006, the surgical hub 15002 can detect collisions or potential collisions of tracked objects. For example, using any combination of the various tracking techniques disclosed herein (e.g., imaging device(s) 15010, structured light sensor(s) 15012, LIDAR sensor(s) 15014, floor sensor(s) 15016, acoustic sensor(s) 15018, fiducial marker(s) 15020, user/device sensor(s) 15022, and GPS 15024), the surgical hub 15002 can detect a potential collision between a portion of a surgical instrument and a critical structure within the surgical field. As another example, the surgical hub 15002 can be configured to detect a potential collision between multiple surgical instruments. As yet another example, the surgical hub 15002 can be configured to detect a potential collision between various other objects in the surgical field. The detected potential collisions and/or detected collisions may not be within the field of view of imaging device(s) 15010, and therefore, may not be viewable by OR staff. Based on the detected potential collisions and/or detected collisions, the surgical hub 15002 can cause display device (e.g., AR device 66) to display a notification, such as an overlay with information related to the collision. In one aspect, the notification can include a warning and/or other instructions for avoiding the collisions. In another aspect, the notification can include an overlay with a graphical representation of the objects involved in the collision. Accordingly, OR staff can perceive and act upon potential collisions and collisions that are not within the field of view of the imaging device(s) 15010.

In another aspect, based on data from the tracking system 15006, the surgical hub 15002 can detect unintended interactions of tracked objects. For example, similar to detecting potential collisions, the surgical hub 15002 can detect an unintended interaction between a portion of a surgical instrument and a critical structure within the surgical field. As another example, the surgical hub 15002 can detect an unintended interaction between multiple surgical instruments. As yet another example, the surgical hub 15002 can detect unintended interactions between various other objects in the surgical field. The detected unintended interactions may not be within the field of view of imaging device(s) 15010, and therefore, may not be viewable by OR staff. Based on the detected unintended interaction, the surgical hub 15002 can cause the display device (e.g., AR device 66) to display a notification, such as an overlay with information related to the unintended interaction, a warning and/or other instructions for avoiding the interaction, and/or an overlay with a graphical representation of the objects involved in the interaction. Accordingly, OR staff can perceive and act upon unintended interaction that are not within the field of view of the imaging device(s) 15010. In some aspects, the surgical hub 15002 can prevent the operation of instruments based on the detected unintended interaction.

For example, a user may be using a monopolar energy device. The tracking system 15006 and/or surgical hub 15002 may detect that the monopolar energy device is proximate to a metallic object (e.g., another surgical instrument, an object in the surgical field, etc.). The surgical hub 15002 can determine that there is a potential unintended interaction between the monopolar device and the metallic object because activating the monopolar device proximate to the metallic object may cause arcing. Based on the detected unintended interaction, the surgical hub 15002 may cause an AR display device 66 to display an overlay warning of the interaction. In another aspect, the surgical hub 15002 may prevent the activation of the monopolar energy device. In yet another aspect, the surgical hub 15002 can cause an overlay to be displayed instructing the user to redirect the energy direction to the intended therapeutic zone. In some aspects, the notifications, warnings, and/or overlays displayed based on detected potential collisions, detected collisions, detected unintended interactions, and other detected interactions between objects can include attributes of an object involved in the interaction. The attributes of the object may be based on instrument data received by the surgical hub 15002 and/or based on tracking data from the tracking system 15006. For example, a force, speed, impact, and/or physical magnitude of interactions between objects may be displayed as overlays. In other aspects, the notifications, warnings, and/or overlays may include a graphic indicating a location of the interaction. Accordingly, a user viewing this graphic may adjust the field of view of an imaging device to view the interaction.

In another aspect, based on data from the tracking system 15006, the surgical hub 15002 can cause graphic overlays to be displayed by a display device (e.g., AR device 66) to assist a user performing a step of a surgical procedure. In one aspect, the overlay can include a graphical representation and/or indicator for an object that is outside of the field of view of an imaging device 15010 capturing an image of the surgical field. The graphic overlay can provide information related to the location and/or other attributes of the object that is out of view. For example, a surgeon may be performing a procedure using a circular stapler. The procedure may involve attaching a device deck of the stapler to a separate anvil portion. The device deck of the stapler may be within the field of view whereas the anvil may be outside of the field of view (e.g., outside of the field of view based on the camera angle, outside of the field of view because tissue is obstructing the view of the anvil, etc.). The surgical hub 15002 can cause the display device to display a rendered image or other graphical representation of the anvil (e.g., indicating the off-image position of the anvil, overlaying a rendered image of the anvil over the obstructing tissue, etc.). In another aspect, the surgical hub 15002 can cause the display device to display a directional indicator overlay showing the direction and/or route that tissue may be manipulated to optimize the attachment of the anvil to the device deck. Thus, the overlay can assist the surgeon in perceiving how objects outside of the field of view of the imaging device 15010 can be manipulated to more easily achieve a desired outcome of the step of the surgical procedure.

Figure 17A:
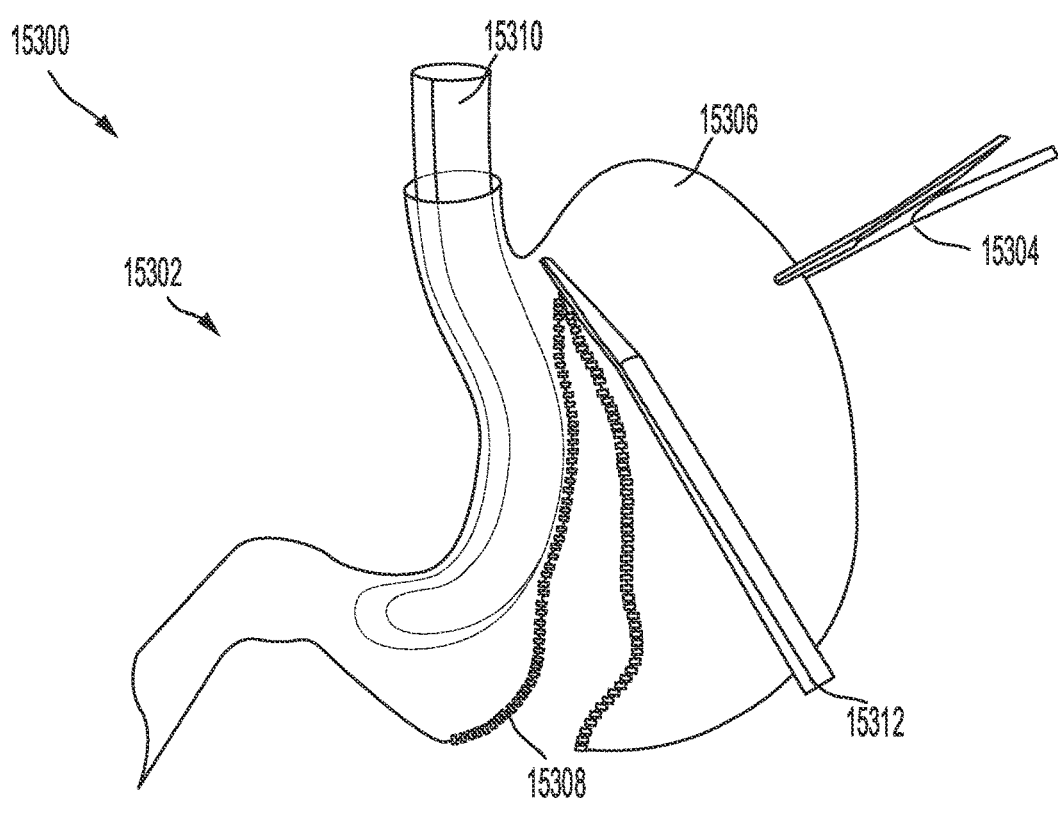
FIGS. 17A and 17B illustrate exemplary intraoperative displays including an image of stomach tissue as a surgeon makes a cut line in the stomach tissue using an endo-cutter, according to one aspect of this disclosure.
Figure 17B:
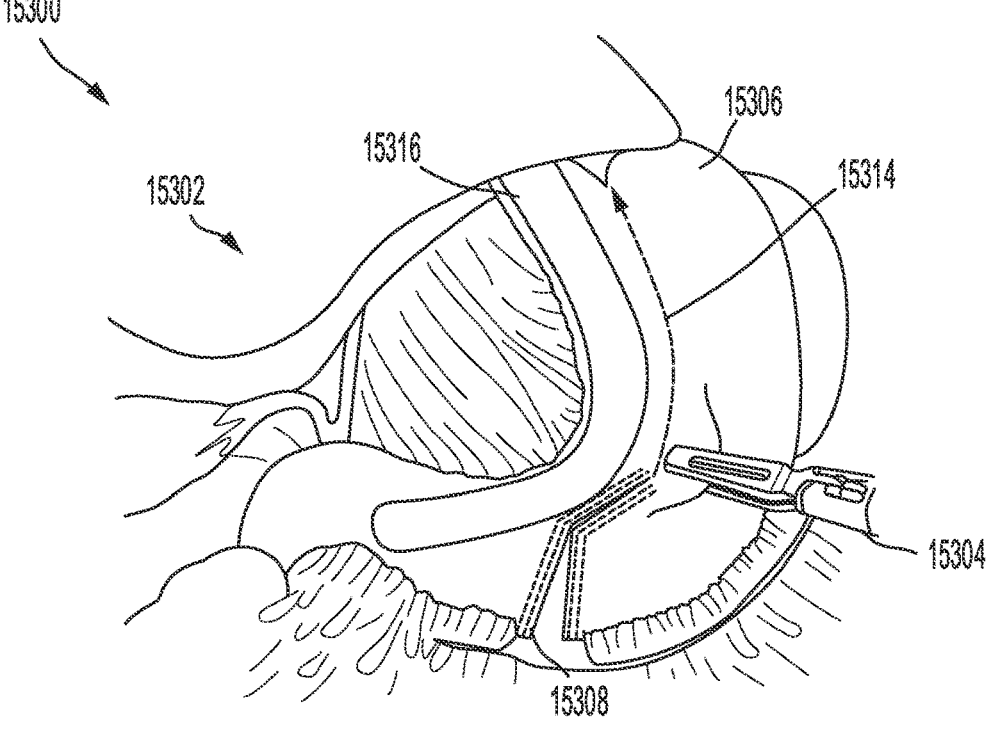

In another aspect, based on data from the tracking system 15006, the surgical hub 15002 can cause graphic overlays to be displayed by a display device (e.g., AR device 66) that may replace the need to use various instruments. For example, FIGS. 17A and 17B illustrate exemplary intraoperative displays 15300 showing the surgical field 15302 during the cutting of stomach tissue 15306, according to at least one non-limiting aspect of the present disclosure. The intraoperative displays 15000 can be displayed by any of the display devices (e.g., AR device 66) disclosed herein. Referring to FIG. 17A, a bougie tube 15310 has been inserted into the patient to provide a guide as a surgeon makes a cut line 15308 in the stomach tissue 15306 using an endo-cutter 15312, assisted by a surgical grasper 15304. Referring now to FIG. 17B, the bougie tube 15310 is no longer being used. Instead, in one aspect, a graphical overlay of a virtual bougie 15316 can be displayed by the intraoperative display 15300 to provide a guide to the surgeon for cutting the stomach tissue 15306. In another aspect, a graphical overlay of a cut-line guide 15314 can be displayed by the intraoperative display 15300 to provide a guide to the surgeon. Thus, the graphical overlay 15314, 15316 can replace the need to physically install the bougie tube 15310 in the patient.

Figure 18:
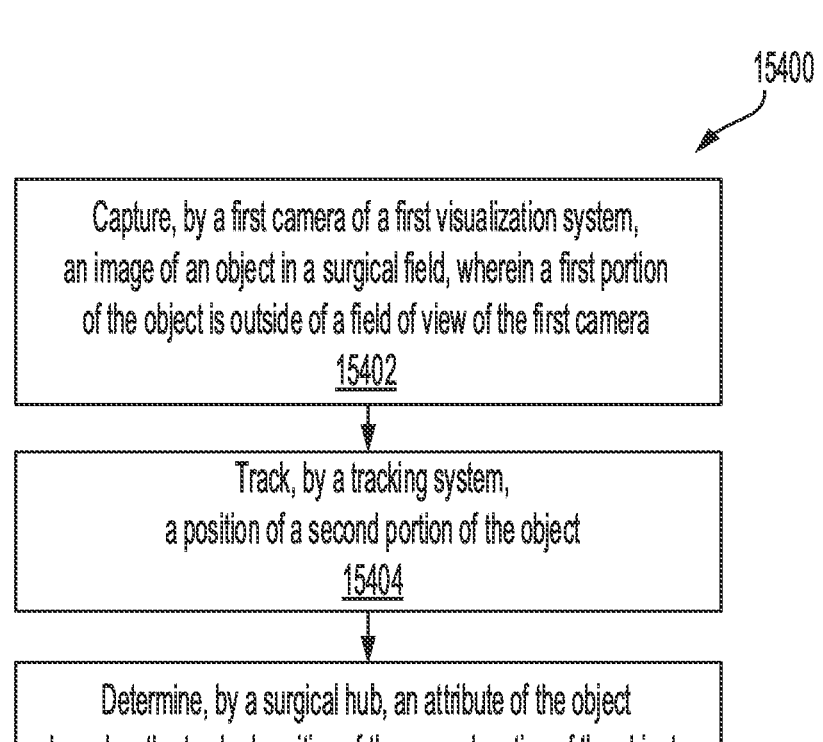
FIG. 18 illustrates a method for mixed reality visualization of a surgical system, according to one aspect of this disclosure.

FIG. 18 illustrates a method 15400 for mixed reality visualization of a surgical system, according to several non-limiting aspects of this disclosure. The method 15400 may be practiced by any combination of the surgical systems, surgical hubs, tracking systems, visualization systems, augmentation systems, AR devices, any of the components thereof, and any other devices and systems disclosed herein, such as surgical systems 1, 2, 50, 52, 15000, surgical hubs 6, 56, 5104, 15002, tracking system 15006, visualization system 8, 15008, communication system 63, augmentation system 83, and AR devices 66, 84.

In accordance with the method 15400, a first camera of a first visualization system can capture 15402 of an image of an object in a surgical field, wherein a first portion of the object is outside of a field of view of the first camera. A tracking system can track 15404 a position of a second portion of the object. A surgical hub can determine 15406 an attribute of the object based on the tracked position of the second portion of the object, wherein the attribute of the object is related to the first portion of the object outside of the field of view of the camera. An augmented reality display device can display 15408 the captured image of the object in the surgical field and a graphic based on the attribute of the object. In one aspect, the object can comprise a surgical instrument, patient issue, a user, or a combination thereof.

In accordance with one aspect of the method 15400, determining 15406 the attribute of the object based on the tracked position of the second portion of the object can include determining a position of the first portion of the object. Further, displaying 15408 the graphic can include the augmented reality display device displaying a rendered image of the first portion of the object.

In another aspect of the method 15400, the tracking system can include the visualization system. Further, the visualization system can include a second camera. Tracking 15404 the position of the second portion of the object can include the second camera capturing an image of the second portion of the object. The second portion of the object may be outside of the field of view of the first camera. In another aspect of the method 15400, tracking 15404 the position of the second portion of the object can include tracking the second portion of the object using a structured light sensor, a light detection and ranging (LIDAR) sensor, radio frequency identification (RFID), global position system (GPS) tracking, audio beaconing, non-visual light tracking, or a combination thereof.

In another aspect of the method 15400, the tracking system can track a position of a structure in the surgical field. Further, determining 15406 an attribute of the object based on the tracked position of the second portion of the object can include the surgical hub identifying an interaction of the first portion of the object and the structure. In one aspect, the augmented reality display device can display a graphic based on the position of the structure. In another aspect, displaying the graphic based on the position of the structure can include displaying an alert based on the identified interaction of the first portion of the object and the structure. In yet another aspect, displaying the graphic based on the position of the structure can include displaying a force of the interaction, a speed of the interaction, an indication of an impact of the first portion of the object and the structure, an energized condition of the object, a time, or a combination thereof.

In another aspect of the method 15400, the object can include a surgical instrument including a fiducial marker. In this aspect, tracking 15404 the position of the second portion of the object can include the tracking system tracking the fiducial marker. In another aspect, the surgical hub can determine a range of motion of the surgical instrument based on the tracked fiducial marker. Further, displaying 15408 the graphic can include the augmented reality display device displaying a rendered image representing the range of motion of the surgical instrument.

Displaying Device-Specific Information and
Managing Devices Use Across Networks

As explained throughout this disclosure, various devices and instruments can be used to perform surgical procedures. These devices can vary widely. For example, devices can have different device types and different device versions, each with different features and intended uses. In some cases, the features and intended uses of devices may be updated by the device manufacturer. Moreover, device manufacturers may develop new techniques for existing devices or release software updates related to device operation. In other cases, devices may be recalled by the manufacture. In yet other cases, counterfeit devices or counterfeit device components can exist that should not be used. Thus, there is an abundance of device identification-related information that OR staff members need to be aware of when using devices for surgical procedures.

Moreover, there is an abundance of device operation-related information that OR staff members must consider when using devices. For example, device performance may deteriorate over time based on repeated use. As another example, devices can be over-used or misused during the course of a surgical procedure. Yet further, devices may sense information that users may not be aware of or know how to easily access. Accordingly, there is a need for apparatuses, system, and methods for managing device-related information and for allowing users to easily access relevant device-related information.

In various aspects, apparatuses, systems, and methods for managing device-related information are disclosed herein. As explained above, devices and surgical instruments may be communicatively connected to a surgical hub (e.g., device/instrument 21 can be connected to surgical hub 56 of FIG. 5). Thus, the surgical hub can be configured to receive device-related information from various devices used with various surgical systems. Moreover, the surgical hub can be communicably coupled a hospital network and/or a network of the device manufacturer. For example, referring to FIG. 5, a computer-implemented interactive surgical system 50 can include one or more surgical systems 52 that include at least one surgical hub 56 in communication with a cloud 54 that may include a remote server 63. In one aspect, the cloud 54 and/or remote server 63 can be associated with a hospital network. The hospital network may be in communication with a device manufacturer database. In another aspect, the cloud 54 and/or remote server 63 can be associated with the device manufacturer database.

In some aspects, devices/instruments 21 connected to a surgical hub 56 can be authenticated based on communication with the hospital network and/or the device manufacturer database. The hospital network can be configured to determine if a connected device/instruments 21 is authorized. For example, a counterfeit device that is attempting to connect to a surgical hub 56 may not be authorized. In one aspect, the hospital network may communicate with a manufacturer database to determine that the counterfeit device is not authorized. As another example, a recalled device attempting to connect to the surgical hub 56 may not be authorized. A device/instrument 21 that is not authorized may be blocked from use, for example by the surgical hub 56.

In one aspect, the authorization of a device/instrument 21 of the device can be verified during a surgical procedure. In another aspect, the authorization of a device/instrument can be verified at a time the device/instrument 21 and/or components of the device (e.g., reload cartridges, replacement components) are stocked. In yet another aspect, the surgical hub 56 may be configured to allow a procedure to proceed even if a device/instrument 21 has not been authorized. For example, a procedure may be allowed to proceed without device/instrument authorization if the lack of authorization is due to the hospital network being down.

In some aspects, connected devices/instruments 21 can store information related to techniques for using the device, intended uses, and/or software updates. This information may be communicated to the surgical hub 56 and stored by the hospital network (e.g., server 63). In other aspects, information related to techniques for using the device, intended uses, and/or software updates may be accessed on the device manufacturer's database upon the connection of the device. Instructions and/or intended uses for device/instruments may be presented to the user of the device via a display device (e.g., AR device 66).

In some aspects, the hospital network and/or the device manufacturer database can store information related to recommended and/or intended device usage. This device usage information can be used to determine if a specific device/instrument 21 has exceeded a recommended use. For example, device usage information can include a maximum recommended usage during a specific period of time (e.g., a device may not be intended to be used for longer than a specified time period, a device may not be intended to be activated more than a specified number of times over a specific time period, etc.). As another example, device usage information can include a maximum recommended number of activations and/or maximum usage time over the course of the lifetime of the device. As another example, device usage information can include intended uses for a specific device/instrument 21. Based on this device usage information, the surgical hub 56 can be configured to alert a user (e.g., via a display device, such as AR device 66) of a detected overuse and/or misuse. In other aspects, the surgical hub 56 can be configured to prevent further use of a device based on device usage information stored by the hospital network and/or the device manufacturer database.

In various aspects, apparatuses, systems, and methods for allowing users to easily access relevant device-related information are disclosed herein. Referring still to FIG. 5, and also to FIG. 8, a user using a device/instrument 21 connected to the surgical hub 56 can request that a display device (e.g., hub display 65, instrument display 50, AR device 66, etc.) display device information related to the device/instrument 21. For example, the surgeon may provide a verbal prompt detected by a microphone associated with the surgical hub 56 to requesting that device information be displayed (e.g., the surgeon may say "show me information"). The user's request that device information be displayed can cause the surgical hub 56 to cause the display device to display information related to the device/instrument 21.

In various aspects, the information displayed related to the device/instrument 21 may include information related to the historic usage of the device and other information related to the current operation of the device. In some aspects, the information displayed can vary depending on the type of device. In one aspect, if the device/instrument 21 is an energy device, the information displayed can include, for example, a number of activations, a total time of activation, a residual temperature at the jaw, an estimated wearing condition of the device, device-specific calibration and/or characterization information which may affect the best usage, a device parameters of interest, or a combination thereof. In another aspect, if the device/instrument 21 is an endo-cutter, the information displayed can include, for example, a number of firings, estimated anvil decambering information, a high/low on tissue gap based on firing on test skin in build, device parameters of interest (e.g., maximum articulation angle, jaw temperature etc.), or a combination thereof. Thus, a user of the device may be able to easily determine if the device is nearing or has exceeded its recommended lifetime (e.g., based on the displayed usage history). The user may also be able to easily access important parameters related to the operation of the device to assist with decision making during a surgical procedure.

Various additional aspects of the subject matter described herein are set out in the following numbered examples:

Example 1: A method for mixed reality visualization of a surgical system, the method comprising: capturing, by a first camera of a first visualization system, an image of an object in a surgical field, wherein a first portion of the object is outside of a field of view of the first camera; tracking, by a tracking system, a position of a second portion of the object; determining, by a surgical hub, an attribute of the object based on the tracked position of the second portion of the object, wherein the attribute of the object is related to the first portion of the object outside of a field of view of the camera; and displaying, by an augmented reality display device, the captured image of the object in the surgical field and a graphic based on the attribute of the object; wherein the object comprises a surgical instrument, patient tissue, or a user, or a combination thereof.

Example 2: The method of example 1, wherein determining the attribute of the object based on the tracked position of the second portion of the object comprises determining a position of the first portion of the object; and wherein displaying the graphic comprises displaying, by the augmented reality display device, a rendered image of the first portion of the object.

Example 3: The method of any of examples 1-2, wherein the tracking system comprises the visualization system; wherein the visualization system comprises a second camera; wherein tracking the position of the second portion of the object comprises capturing, by the second camera, an image of the second portion of the object; and wherein the second portion of the object is outside of the field of view of the first camera.

Example 4: The method of any of examples 1-3, wherein tracking, by the tracking system, the position of the second portion of the object comprises tracking the second portion of the object using a structured light sensor, a light detection and ranging (LIDAR) sensor, radio frequency identification (RFID), global position system (GPS) tracking, audio beaconing, non-visual light tracking, or a combination thereof.

Example 5: The method of any of examples 1-4, further comprising tracking, by the tracking system, a position of a structure in the surgical field; wherein determining the attribute of the object based on the tracked position of the second portion of the object comprises identifying, by the surgical hub, an interaction of the first portion of the object and the structure.

Example 6: The method of any of examples 1-5, further comprising displaying, by the augmented reality display device, a graphic based on the position of the structure.

Example 7: The method of any of examples 1-6, wherein displaying the graphic based on the attribute of the object comprises displaying, by the augmented reality display device, an alert based on the identified interaction.

Example 8: The method of any of examples 1-7, wherein displaying the graphic based on the attribute of the object comprises displaying, by the augmented reality display device, a force of the interaction, a speed of the interaction, an indication of an impact of the first portion of the object and the structure, an energized condition of the object, a time, or a combination thereof.

Example 9: The method of any of examples 1-8, wherein the object comprises a surgical instrument comprising a fiducial marker; and wherein tracking the position of the second portion of the object comprises tracking, by the tracking system, the fiducial marker.

Example 10: The method of any of examples 1-9, further comprising determining, by the surgical hub, a range of motion of surgical instrument based on the tracked fiducial marker; wherein displaying the graphic comprises displaying, by the augmented reality display device, a graphic representing the range of motion of the surgical instrument.

Example 11: A surgical system for mixed reality visualization, the system comprising: a first visualization system comprising a first camera configured to capture an image of an object in a surgical field, wherein a first portion of the object is outside of a field of view of the camera; a first tracking system configured to track a position of a second portion the object; a surgical hub configured to determine an attribute of the object based on the tracked position of the second portion the object, wherein the attribute of the object is related to the first portion of the object outside of a field of view of the camera; and an augmented reality display device configured to display the captured image of the object in the surgical field and a graphic based on the attribute of the object; wherein the object comprises a surgical instrument, patient tissue, a user, or a combination thereof.

Example 12: The system of example 11, wherein the attribute of the object comprises a position of the first portion of the object; and wherein the graphic comprises a rendered image of the first portion of the object.

Example 13: The system of any of examples 11-12, wherein the tracking system comprises the visualization system; wherein the visualization system comprises a second camera configured to capture an image of the second portion of the object; and wherein the second portion of the object is outside of the field of view of the first camera of the first visualization system.

Example 14: The system of any of examples 11-13, wherein the tracking system uses a structured light sensor, a light detection and ranging (LIDAR) sensor, radio frequency identification (RFID), global position system (GPS) tracking, audio beaconing, non-visual light tracking, or a combination thereof.

Example 15: The system of any of examples 11-14, wherein the tracking system is configured to track a position of a structure in the surgical field; wherein the surgical hub is configured to identify an interaction of the first portion of the object and the structure; and wherein the attribute of the object comprises the identified interaction.

Example 16: The system of any of examples 11-15, wherein the augmented reality display device is configured to display a graphic based on the position of the structure.

Example 17: The system of any of examples 11-16, wherein the graphic based on the attribute of the object comprises an alert based on the identified interaction.

Example 18: The system of any of examples 11-17, wherein the graphic based on the attribute of the object comprises a force of the interaction, a speed of the interaction, an indication of an impact of the first portion of the object and the structure, an energized condition of the object, a time, or a combination thereof.

Example 19: The system of any of examples 11-18, wherein the object comprises the surgical instrument; wherein the surgical instrument comprises a fiducial marker; and wherein tracking system is configured to track the fiducial marker.

Example 20: The system of any of examples 11-19, wherein the surgical hub is configured to determine a range of motion of surgical instrument based on the tracked fiducial marker; wherein the attribute of the object comprises the range of motion of the surgical instrument; and wherein the graphic based on the attribute of the object comprises a graphic representing the range of motion of the surgical instrument.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for mixed reality visualization of a surgical system, the method comprising:
    obtaining an image of a surgical instrument in a surgical field via an imaging device, wherein a first portion of the surgical instrument is outside a field of view of the imaging device and wherein a second portion of the surgical instrument is within the field of view of the imaging device;
    tracking a position of the second portion of the surgical instrument within the field of view of the imaging device;
    determining, based on the position of the second portion of the surgical instrument, an interaction between the surgical instrument and an object, wherein the interaction is outside the field of view of the imaging device;
    determining an operating parameter associated with the first portion of the surgical instrument that is outside the field of view of the imaging device, wherein the operating parameter is determined based on the interaction between the surgical instrument and the object;
    rendering an element based on the operating parameter and the interaction, wherein the element is associated with the first portion of the surgical instrument that is outside the field of view of the imaging device; and
    displaying a blended image, wherein the blended image comprises the obtained image and the element.

2. The method of claim 1, wherein the position is tracked based on data associated with at least one of: a structured light sensor, a light detection and ranging (LIDAR) sensor, radio frequency identification (RFID), audio beaconing, or non-visual light tracking.

3. The method of claim 1, wherein the object is a second surgical instrument, and wherein the element indicates that the interaction is an unintended collision between the surgical instrument and the second surgical instrument occurring outside the field of view of the imaging device.

4. The method of claim 1, wherein the surgical instrument comprises a fiducial marker, and wherein tracking the position of the second portion of the surgical instrument is tracked via the fiducial marker.

5. The method of claim 4, wherein the method further comprises:
    determining the operating parameter further based at least on the fiducial marker, wherein the operating parameter is associated with a range of motion of the surgical instrument, and wherein the element indicates the range of motion of the surgical instrument.

6. A surgical system for mixed reality visualization, the surgical system comprising:
    a processor configured to:
        obtain an image of a surgical instrument in a surgical field via an imaging device, wherein a first portion of the surgical instrument is outside a field of view of the imaging device and wherein a second portion of the surgical instrument is within the field of view of the imaging device;
        track a position of the second portion of the surgical instrument within the field of view of the imaging device;
        determine, based on the position of the second portion of the surgical instrument, an interaction between the surgical instrument and an object;
        determine an operating parameter associated with the first portion of the surgical instrument that is outside the field of view of the imaging device, wherein the operating parameter is determined based on the interaction between the surgical instrument and the object;
        render an element based on the operating parameter and the interaction, wherein the element is associated with the first portion of the surgical instrument that is outside the field of view of the imaging device; and display a blended image, wherein the blended image comprises the obtained image and the element.

7. The surgical system of claim 6, wherein the position is tracked based on data associated with at least one of: a structured light sensor, a light detection and ranging (LI-DAR) sensor, radio frequency identification (RFID), audio beaconing, or non-visual light tracking.

8. The surgical system of claim 6, wherein the object is a second surgical instrument, and wherein the element indicates that the interaction is an unintended collision between the surgical instrument and the second surgical instrument occurring outside the field of view of the imaging device.

9. The surgical system of claim 6, wherein the surgical instrument comprises a fiducial marker, and wherein the position of the second portion the surgical instrument is tracked via the fiducial marker.

10. The surgical system of claim 9, wherein the processor is further configured to;

determine the operating parameter further based at least on the fiducial marker, wherein the operating parameter is associated with a range of motion of the surgical instrument, and wherein the element indicates the range of motion of the surgical instrument.

11. The method of claim 1, wherein the operating parameter is at least one of a speed, a force, a firing speed, a firing force, an activation status, a power level, an activation time, or an energy mode associated with the surgical instrument.

12. The surgical system of claim 6, wherein the operating parameter is at least one of a speed, a force, a firing speed, a firing force, an activation status, a power level, an activation time, or an energy mode associated with the surgical instrument.

13. The method of claim 1, wherein the operating parameter is a force associated with the interaction, and wherein the element indicates the force of the interaction.

14. The method of claim 1, wherein the operating parameter is a speed associated with the interaction, and wherein the element indicates the speed of the interaction.

*    *    *    *    *